US 8,734,406 B2
May 27, 2014

(12) United States Patent
Cressman

(10) Patent No.: US 8,734,406 B2
(45) Date of Patent: May 27, 2014

(54) METHODS AND SYSTEMS FOR CHEMICAL ABLATION

(75) Inventor: Erik N. K. Cressman, Lake Elmo, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 47 days.

(21) Appl. No.: 13/511,852

(22) PCT Filed: Nov. 23, 2010

(86) PCT No.: PCT/US2010/057800
§ 371 (c)(1),
(2), (4) Date: May 24, 2012

(87) PCT Pub. No.: WO2011/066278
PCT Pub. Date: Jun. 3, 2011

(65) Prior Publication Data
US 2012/0253192 A1    Oct. 4, 2012

Related U.S. Application Data

(60) Provisional application No. 61/263,961, filed on Nov. 24, 2009.

(51) Int. Cl.
*A61M 5/00*    (2006.01)

(52) U.S. Cl.
USPC ............. 604/257; 604/113; 604/506; 606/27

(58) Field of Classification Search
USPC .................. 604/257, 506–507, 113; 600/431; 606/27
See application file for complete search history.

(56) References Cited

U.S. PATENT DOCUMENTS

| 5,045,056 | A  | 9/1991  | Behl |
| 5,797,869 | A  | 8/1998  | Martin et al. |
| 6,165,201 | A  | 12/2000 | Sawhney et al. |
| 6,626,902 | B1 | 9/2003  | Kucharczyk et al. |
| 6,824,555 | B1 | 11/2004 | Towler |
| 6,958,059 | B2 | 10/2005 | Zadno-Azizi |
| 8,343,095 | B2 | 1/2013  | Cressman |
| 8,585,691 | B2 | 11/2013 | Cressman |
| 2002/0120238 | A1 | 8/2002  | McGuckin, Jr. et al. |
| 2002/0143302 | A1 | 10/2002 | Hinchleffe et al. |
| 2003/0187411 | A1 | 10/2003 | Constantz |
| 2003/0226566 | A1 | 12/2003 | Dhuper |
| 2004/0166062 | A1 | 8/2004  | Roberts et al. |
| 2005/0187542 | A1 | 8/2005  | Auge, II et al. |

(Continued)

FOREIGN PATENT DOCUMENTS

| JP | 2002502278 A | 1/2002 |
| JP | 2005506101 A | 3/2005 |

(Continued)

OTHER PUBLICATIONS

Authorized Officer S. Koleva. International Search Report and Written Opinion in International Application No. PCT/US2009/052033, dated Nov. 30, 2009, 20 pages.

(Continued)

*Primary Examiner* — Theodore Stigell
(74) *Attorney, Agent, or Firm* — Fish & Richardson P.C.

(57) ABSTRACT

Thermochemical ablation techniques may provide ablation of bodily tissue using chemical reaction energy.

20 Claims, 21 Drawing Sheets

(56) References Cited

U.S. PATENT DOCUMENTS

| | | | |
|---|---|---|---|
| 2006/0079869 | A1 | 4/2006 | Bischof et al. |
| 2007/0191781 | A1 | 8/2007 | Richards et al. |
| 2008/0171982 | A1 | 7/2008 | Mehier |
| 2011/0152852 | A1 | 6/2011 | Cressman |
| 2013/0131659 | A1 | 5/2013 | Cressman |

FOREIGN PATENT DOCUMENTS

| | | | |
|---|---|---|---|
| WO | WO9852480 A1 | | 11/1998 |
| WO | WO0009199 A1 | | 2/2000 |
| WO | WO02067796 A1 | | 9/2002 |
| WO | WO03080151 A2 | | 10/2003 |
| WO | 2008/106357 | | 9/2008 |
| WO | WO 2008/106357 | | 9/2008 |
| WO | WO2008/106357 | * | 9/2008 |
| WO | WO2008108357 A1 | | 9/2008 |
| WO | WO 2010/014658 | | 2/2010 |

OTHER PUBLICATIONS

Authorized Officer A. Wittmann-Regis. International Preliminary Report on Patentability in International Application No. PCT/US2009/052033, dated Feb. 10, 2011, 11 pages.

Authorized Officer M. Honda. International Preliminary Report on Patentability in International Application No. PCT/US2008/054556, mailed Sep. 11, 2009, 6 pages.

Authorized Officer S. Oh. International Search Report and Written Opinion in International Application No. PCT/US2008/054556, mailed Jul. 28, 2008, 12 pages.

Authorized Officer P. Becamel. International Preliminary Report on Patentability in International Application No. PCT/US2010/057800, mailed Jun. 7, 2012, 7 pages.

Authorized Officer H. Kang. International Search Report and Written Opinion in International Application No. PCT/US2010/057800, dated Aug. 2, 2011, 11 pages.

Araki et al., "Hepatocellular carcinoma treated by percutaneous hot saline injection," *Oncology Reports*, 2004, 12: 569-571.

Arrivé et al., "Percutaneous Acetic Acid Injection for Hepatocellular Carcinoma: Using CT Fluroscopy to Evaluate Distribution of Acetic Acid Mixed with an Iodinated Contrast Agent," *American Roentgen Ray Society*, AJR:180, Jan. 2003.

Castaneda et al., "Cytotoxicity of millimolar concentrations of ethanol on HepG2 human tumor cell line compared to normal rat hepatocytes in vitro," *J. Cancer Res. Clin. Oncol.*, 2000, 126(9):503-510.

Castaneda et al., "Short exposure to millimolar concentrations of ethanol induces apoptotic cell death in multicellular HepG2 spheroids," *J. Cancer. Res. Clin. Oncol.*, 2000, 126(6):305-310.

Clark et al., "Chemical Ablation of Hepatocellular Carcinoma," *JVIR*, 2002, 13(9): S246-S252, Part 2.

Clark et al., "Chemical Ablation of Liver Cancer," *Techniques in Vascular and Interventional Radiology*, 2007, 10(1):58-63.

Cressman, E.N.K., "A New Hydrophobic Gel Phantom Gel for Study of Thermochemical Ablation: Initial Results Using a Weak Acid and Weak Base," Abstract 434, p. S154, *2007 SIR Annual Scientific meeting*, Mar. 1-6, 2007, Seattle, WA.

Finch, et al., "The use of a 'Liquid' Electrode in Hepatic Electrolysis," *Journal of Surgical Research*, 2004, 120:272-277.

Frank et al., Exothermic Electrophiles for Thermochemical Ablation Assessed in a Gel Phantom,: *SIR 2008 Annual Scientific Meeting*, Abstract No. 278, 1 page.

Glinos, et al., "Cytokinetic and Cytotoxic Effects of Urea on HeLa Cells in Suspension Cultures," *J. Nat'l Cancer Inst.*, 1982, 71:1211-1219.

Goldberg et al., "Radio-Frequency Thermal Ablation with NaCl Solution Injection: Effect of Electrical Conductivity on Tissue Heating and Coagulation—Phantom and Porcine Liver Study," *Radiology*, 2001, 219:157-165.

Hiltbrand et al. "A New Method of Thermoablation with Hot Water Vapour for Localized Tumours," *Anticancer Research*, 2004, 24(5A):2757-2763.

Kurokohchi et al. "Percutaneous ethanol and lipiodol injection therapy for hepatocellular carcinoma," *International Journal of Oncology*, 2004, 24: 381-387.

Liao et al., "Radiofrequency ablation after transarterial embolization as therapy for patients with unresectable hepatocellular carcinoma," *EJSO, Journal of Cancer Surgery*, 2008, 34:61-64.

Lubienski et al. "Radiofrequency Thermal Ablation: Increase in Lesion Diameter with Continuous Acetic Acid Infusion" *Cadiovasc Intervent Radiol.*, 2005, 28:789-794.

Nanz, et al., "Contrast Material—enhanced Visualization of the Ablation Medium for Magnetic Resonance—monitored Ethanol Injection Therapy: Imaging and Safety Aspects," *J. Vascular and Interventional Radiology*, 2006, 17(1): 95-102.

Parmley, et al., "The Possible Deleterious Effects of the Intramymetrial Injection of Hypertonic Urea," *Obstetrics & Gynecology*, 1975, p. 210-212.

Puls, et al., "Laser-Induced Thermotherapy (LITT) of Liver metastases: MR-Guided Percutaneous Insertion of an MRI-compatible Irrigated Microcatheter System Using a Closed High-Field Unit," *Journal of Magnetic Resonance Imaging*, 2003, 17:663-670.

Weinberg et al., "Combined radiofrequency ablation and doxorubicin-eluting polymer implants for liver cancer treatment," *J of Biomed Mater. Res. Part A*, 2006, p. 205-213.

Wilson, "A Renaissance for Hofmeister," *Chemical & Engineering News: Science & Technology*, 2007, 85(48):47-49.

Young, et al., "Combined Radiofrequency Ablation and Hot Saline Injection in Rabbit Liver," *Investigative Radiology*, 2003, 38(11):725-732.

Kim et al., "Combined radiofrequency ablation and hot saline injection in rabbit liver," Invest Radiol., 38(11):725-732, Nov. 2003.

* cited by examiner

METHODS AND SYSTEMS FOR CHEMICAL ABLATION

CROSS REFERENCE TO RELATED APPLICATIONS

This application is a National Stage application under 35 U.S.C. §371 of International Application No. PCT/US2010/057800, having an International Filing Date of Nov. 23, 2010, which claims the benefit of U.S. Provisional Application Ser. No. 61/263,961, filed Nov. 24, 2009. The disclosures of the prior applications are considered part of (and are incorporated by reference in) the disclosure of this application.

TECHNICAL FIELD

This document relates to delivery of chemical reagents to targeted bodily tissue to provide, for example, thermochemical ablation therapy.

BACKGROUND

A number of ablation treatments have been used to treat tumors and other tissue in the body. In some cases, for example, ablation therapy may be used to treat tumors (e.g., tumors that are not responsive to chemotherapy or other treatment techniques). An example is primary liver cancer or hepatocellular carcinoma (HCC), which is an aggressive neoplasm that may not respond well to intravenous chemotherapy.

The choice of treatment for cancers such as HCC normally depends on severity of underlying liver disease, size and number of lesions, location of lesions, ability to detect them with MRI, non-contrast or contrast CT, or ultrasound, and local expertise. Conventionally, physicians have targeted tumor tissue with heat by radiofrequency (RF) ablation, microwave ablation, or combined heating with coadministration of drug-containing liposomes, used cryoablation to freeze tumor tissue, or used hepatic arterial drug infusion, bland arterial embolization, chemotherapy combined with arterial embolization, selective internal radioembolization using radioactive labeled iodized oil or radioactive microspheres as the embolic agent, external beam radiation therapy, or direct injection of a single agent (e.g., ethanol, acetic acid, hydrochloric acid, hot saline, or sodium hydroxide) to ablate tumor tissue.

SUMMARY

Some chemical ablation techniques may provide minimally invasive ablation of solid tumors such as liver cancer, lung cancer, renal cancer, breast cancer, prostate cancer, sarcomas, metastatic disease, or the like. Such techniques also may provide minimally invasive ablation of lumens (e.g., venous ablation for varicose veins and varicoceles). Thermochemical reactions may be induced by mixing, for example, at least one reducing agent and at least one oxidizing agent. Thermochemical reactions also may be induced by administering a reagent that will undergo hydration when it comes into contact with water (e.g., water present in bodily tissues, or added water or aqueous solutions). Such techniques may induce chemical reactions to generate heat for ablation energy (e.g., employing chemical reaction energy rather than electrical energy, magnetic energy, or direct chemical toxic effects), where the chemical reactions provide, for example, a heated solution, suspension, colloid, gel, or the like, with a limited and safe level of reaction products.

Some of the techniques described herein may permit a health care professional (e.g., a physician) to simultaneously infuse at least two thermochemical ablation reagents without mixing the reagents until the reagents reach the distal portion of the delivery cannula. Some techniques may permit a health care professional to administer a thermochemical ablation reagent, or a mixture of thermochemical ablation reagents, that will result in generation of heat after they reach the target site (e.g., via the distal portion of a delivery cannula, or upon implantation at the target site).

Other techniques for ablating tumor tissue may include chemical ablation by denaturation and/or inducement of cell death (e.g., via apoptosis). These methods may include administration of one, two, or more chemical ablation reagents. When multiple reagents are used, they may be administered simultaneously, and may be mixed prior to being taken up in the delivery cannula, or upon reaching the distal portion of the cannula. Such ablation techniques may provide a solution with a limited and safe level of reagents.

Some or all of the embodiments described herein may provide one or more of the following advantages:

The ablation techniques may provide minimally invasive ablation of solid tumors (e.g., liver cancer, lung cancer, renal cancer, breast cancer, prostate cancer, sarcomas, or the like), and also may be useful for treating other tissues including varicoceles, varicose veins, or the like. Such techniques may be useful, for example, to treat patients who are not surgical candidates due to the nature of the tumors or other intervening factors.

The thermochemical ablation techniques may induce chemical reactions to generate heat either to be the primary ablation source or to augment another ablation source (e.g., RF ablation, microwave ablation, denaturant sources such as sclerosants, detergents, or urea, or other ablation sources).

The chemical reactions induced by mixing at least one reducing agent and at least one oxidizing agent, for example, may be highly exothermic at a relatively low reactant concentration, such that lower doses of the reagents may be used to achieve ablation.

Some of the systems and devices described herein may be manufactured without high-cost components such as RF ablation probes or energy source generators/base units. In addition, there may be no need for cables or connecting tubing that would transgress the sterile procedure field to connect to a base power unit, thereby adding convenience and improved procedural safety for the treating health care professional and the patient.

The thermochemical ablation techniques described herein may be used to treat larger tumors in a lower number of treatment sessions, thereby adding convenience to the patient.

The thermochemical ablation process can be monitored in real-time using medical imaging systems, such as ultrasound imaging devices or CT. Moreover, in some embodiments, the thermochemical ablation process can be monitored in an MRI setting without the need for specialized (high-cost), MRI-compatible alloys in the delivery device.

The devices described herein permit a health care professional to simultaneously infuse at least two thermochemical ablation reagents without mixing the reagents until the reagents reach the distal portion of the delivery cannula. As such, some embodiments of the delivery device can be used to provide the ablation heat energy to internal body tissue without the requirement for outer layers of thermal insulation that may otherwise increase the outer size of the delivery device (and the delivery pathway through the tissue).

The delivery cannula may include a number of side ports that provide radial dispersion of, for example, oxidizing and reducing agents when exiting the cannula, thereby promoting mixing (e.g., more turbulence) and distributing the ablation heat energy in a more even manner. Moreover, the reagents can provide an ablative effect that causes more even shaping in the treated area (as compared to a direct injection of acetic acid or ethanol) due to the conductive effects of heat into the surrounding tissue.

In some circumstances, a portion of the reagents (e.g., oxidizing and reducing agents) can mix with one another within the distal portion of the cannula before dispensation into the targeted tissue. By mixing at least a portion of the reagents in the distal portion, some portion of the dispensed fluid can be heated from the exothermic chemical reaction immediately before dispensation into the targeted tissue.

Redox and hydration reactions, or denaturing chemicals such as urea and ethanol, can be effective without shifting the pH at the site of administration. Alternatively, the reagents can be selected and administered in an amount that will alter the pH at the target site.

When a reagent such as a sugar is used as a substrate in a redox reaction, the excess substrate can be metabolized quickly and with little or no adverse effects on the surrounding tissue.

Some reactions can minimize gas formation, resulting in little if any risk of air embolus.

In one aspect, this document features a thermochemical ablation system, comprising: a percutaneous fluid delivery cannula comprising first and second lumens extending from a proximal portion to a distal portion, the distal portion comprising a first side port in fluid communication with at least the first lumen and a second side port in fluid communication with at least the second lumen; a first reservoir that contains a reducing agent so as to communicate the reducing agent through the first lumen to the distal portion of the percutaneous fluid delivery cannula, at least a portion of the reducing agent being deliverable out of the first side port; and a second reservoir that contains an oxidizing agent so as to communicate the oxidizing agent through the second lumen to the distal portion of the percutaneous fluid delivery cannula, at least a portion of the oxidizing agent being deliverable out of the second side port to react with the reducing agent at the distal portion and generate an exothermic redox reaction. The redox reaction can result in a change in oxidation state for the oxidizing and reducing agents. The of claim 1, wherein delivery of the reducing agent from the first side port and the oxidizing agent from the second side port can provide simultaneous radial dispersion of the oxidizing and reducing agents. The exothermic chemical reaction can generate heat to ablate bodily tissue proximate the distal portion of the percutaneous fluid delivery cannula. The reducing agent can be selected from the group consisting of glycerol, dextrin, maltodextrin, glucose, sucrose, hydrogen peroxide, iron(II) ammonium sulfate, titanium trichloride, cuprous chloride, stannous sulfate, and sodium thiosulphate. The reducing agent can have a concentration of about 0.5 M to about 5 M, or about 1 M to about 3 M. The oxidizing agent can be selected from the group consisting of permanganate, sodium hypochlorite, sodium peroxide, iron(II) ammonium sulfate, and ammonium persulfate. The oxidizing agent can have a concentration of about 0.5 M to about 5 M, or about 1 M to about 3 M. The system can further comprise a first actuator to deliver fluid from the first reservoir and a second actuator to deliver fluid from the second reservoir, the first and second actuators being coupled to one another so as to provide simultaneous actuation. The percutaneous fluid delivery cannula can comprise a generally rigid injection needle (e.g., an injection needle having an outside diameter of about 0.134 inches or less), or a flexible catheter.

In another aspect, this document features a method for thermochemical ablation of targeted tissue, comprising: delivering a reducing agent through a first lumen of a percutaneous injection needle; delivering an oxidizing agent through a second lumen of the percutaneous injection needle; simultaneously infusing the oxidizing and reducing agents into targeted tissue to mix the oxidizing and reducing agents at a distal portion of the injection needle, resulting in an exothermic redox reaction between the oxidizing and reducing agents. The redox reaction can result in a change in oxidation state for the oxidizing and reducing agents The reducing agent can be delivered from a first side port of the injection needle and the oxidizing agent can be delivered from a second side port of the injection needle, such that the oxidizing and reducing agents are radially dispersed. The exothermic chemical reaction can generate heat to ablate bodily tissue proximate the distal portion of the injection needle. The reducing agent can be selected from the group consisting of glycerol, dextrin, maltodextrin, glucose, sucrose, hydrogen peroxide, iron(II) ammonium sulfate, titanium trichloride, cuprous chloride, stannous sulfate, and sodium thiosulphate. The reducing agent can have a concentration of about 0.5 M to about 5 M, or about 1 M to about 3 M. The oxidizing agent can be selected from the group consisting of permanganate, sodium hypochlorite, sodium peroxide, iron(11) ammonium sulfate, and ammonium persulfate. The oxidizing agent can have a concentration of about 0.5 M to about 5 M, or about 1 M to about 3 M.

In another aspect, this document features a chemical ablation system, comprising:

a percutaneous fluid delivery cannula comprising a lumen extending from a proximal portion to a distal portion, the distal portion comprising a port in fluid communication with the lumen; and a reservoir containing a combination of denaturing reagents in fluid communication with the lumen of the percutaneous fluid delivery cannula, at least a portion of the reagents being deliverable out of the port so as to denature components of cells present at the targeted site to locally ablate bodily tissue proximate the distal portion of the percutaneous fluid delivery cannula. The combination of reagents can comprise urea and ethanol. The urea can have a concentration of about 0.2 M to about 2 M, or about 0.25 M to about 0.5 M. The ethanol can be about 0.5% to about 3% ethanol, or about 1% to about 2% ethanol. The system can further comprise a real-time imaging system that monitors the distal portion of the percutaneous fluid delivery cannula and the delivery of the reagent. The percutaneous fluid delivery cannula can comprise a generally rigid injection needle (e.g., an injection needle having an outside diameter of about 0.134 inches or less), or a flexible catheter.

In another aspect, this document features a method for chemical ablation of targeted tissue, comprising: delivering two or more denaturants through a lumen of a percutaneous injection needle to a targeted tissue site. The denaturants can be delivered simultaneously or sequentially. The denaturants can be delivered from one or more side ports of the injection needle. The denaturants can comprise urea and ethanol. The urea can have a concentration of about 0.2 M to about 2 M, or about 0.25 M to about 0.5 M. The ethanol can be about 0.5% to about 3% ethanol, or about 1% to about 2% ethanol. The denaturants can further comprise a diagnostic group usable for imaging or tracing purposes. The denaturants can comprise one or more diagnostic leaving groups usable for imaging or tracing purposes.

In still another aspect, this document features a thermochemical ablation system, comprising: a percutaneous fluid delivery cannula comprising a lumen extending from a proximal portion to a distal portion, the distal portion comprising a port in fluid communication with the lumen; a reservoir containing a reagent in fluid communication with the lumen of the percutaneous fluid delivery cannula, at least a portion of the reagent being deliverable out of the port so as to react with water inherently present at the targeted site to locally generate heat sufficient to ablate bodily tissue proximate the distal portion of the percutaneous fluid delivery cannula. The percutaneous fluid delivery cannula can comprise a generally rigid injection needle (e.g., an injection needle having an outside diameter of about 0.134 inches or less), or a flexible catheter. The system can further comprise a real-time imaging system that monitors the distal portion of the percutaneous fluid delivery cannula and the delivery of the reagent This document also features a method for thermochemical ablation of targeted tissue, comprising: delivering a highly reactive reagent through a lumen of a percutaneous injection needle to a targeted tissue site; and reacting the delivered reagent with water at the targeted tissue location to locally generate ablation heat at the targeted tissue site. The highly reactive reagent can be delivered from one or more side ports of the injection needle. The highly reactive reagent can comprise calcium oxide or sulfuric acid. The highly reactive reagent can further comprise a diagnostic group usable for imaging or tracing purposes. The highly reactive reagent can comprise one or more diagnostic. leaving groups usable for imaging or tracing purposes.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Figure 1:
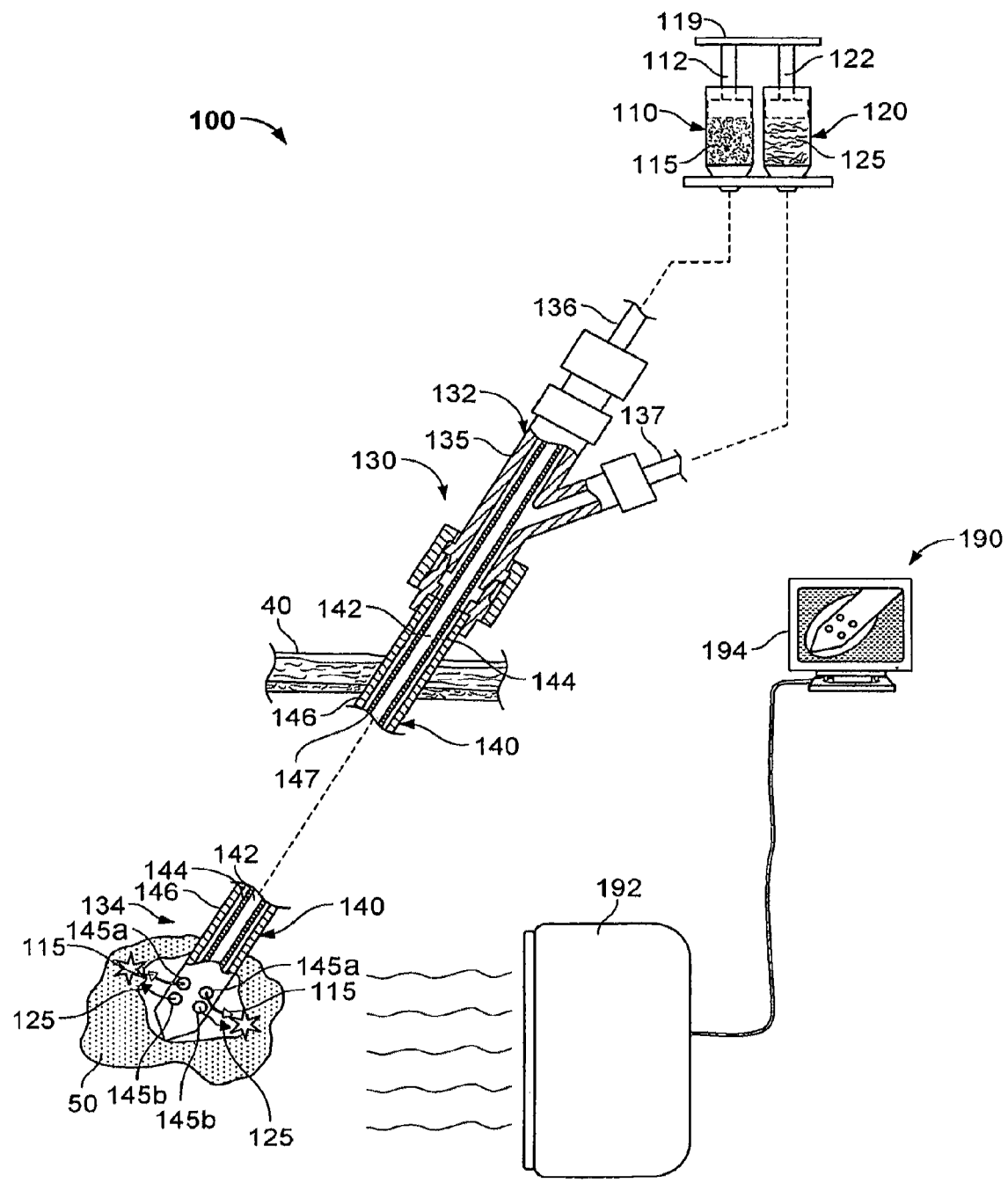
FIG. 1 is a section view of a thermochemical ablation system, in accordance with some embodiments.

A thermochemical ablation system may employ minimally invasive techniques to ablate solid tumors or other targeted tissue. These ablation techniques may induce chemical reactions to generate heat for ablation energy. Such chemical reactions may be induced by mixing a first reagent and a second reagent, such as a reducing agent and an oxidizing agent. Such chemical reactions also may be induced by using a reagent that will undergo a hydration reaction when it comes into contact with water (e.g., water present in bodily tissues). In some embodiments, a thermochemical ablation system enables a health care professional to simultaneously infuse at least two thermochemical ablation reagents without mixing the reagents until the reagents reach the targeted tissue. Chemical ablation techniques also may result in denaturation of tumor cell proteins and apoptosis of tumor cells. For example, a denaturant such as urea, ethanol, or a combination thereof may induce denaturation and apoptosis of tumor cells. When more than one denaturant is administered, the combination may be mixed prior to injection or at the distal end of the injection cannula, for example.

The ablation techniques described herein can be used to treat solid tumors that arise in number of circumstances, including liver cancer, lung cancer, renal cancer, breast cancer, prostate cancer, sarcomas, or the like. These techniques may be useful, for example, to treat patients who are not surgical candidates due to the nature of the tumors or other intervening factors. For example, some patients with HCC or other types of liver cancer are not candidates for surgery. The ablation systems described herein may be effective in the treatment of such liver cancer in a manner that is relatively convenient to the patient (e.g., possibly reducing the number of treatment sessions) and relatively cost-effective for the medical care provider (e.g., not necessarily requiring high-cost equipment such as RF ablation probes or the like). The ablation techniques described herein also can be used to treat other targeted tissue, such as occlusions that arise in bodily passage ways. Further, the ablation techniques described herein are not limited to use in human patients. For example, the ablation systems described herein may be used to treat other animal patients, including mammalian patients.

The techniques described herein may be used in percutaneous treatments. They also may be used as a treatment during open surgery, for example, as a method of intra-operative ablation. In some embodiments, an ablation reagent or a combination of ablation reagents can be administered by injection of a solution or a suspension (e.g., using a system as described herein and shown in FIGS. 1-6). In other cases, an ablation reagent or a combination of ablation reagents can be administered as a gel or a solid (e.g., for reagents that are not readily soluble in water). Other suitable methods for administering an ablation reagent or a combination of reagents as described herein also are contemplated.

1. Thermochemical Ablation Using Redox Reactions

Figure 7:
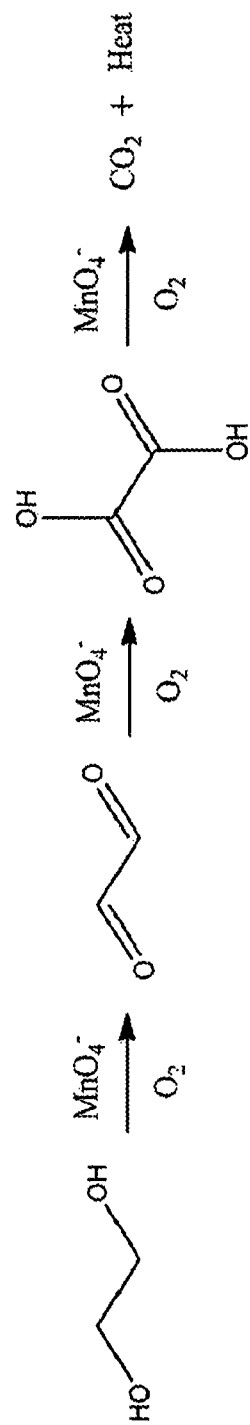
FIG. 7 is a diagram of a redox reaction in which ethylene glycol is oxidized by potassium permanganate.

Thermochemical ablation reagents that are infused into targeted tissue may be selected to provide a suitable energy deposition in the targeted tissue and tissue surrounding the targeted area. For example, the combination of an oxidizing agent with a reducing agent in a redox reaction can result in a powerful release of heat and, in some cases, a metal species. A redox reaction is a chemical reaction in which the oxidation number (oxidation state) of the reagents is changed, wherein oxidation is an increase in oxidation number and reduction is a decrease in oxidation number. In some cases, redox reactions also include the transfer of electrons. Simple redox reactions include the oxidation of carbon to give carbon dioxide, and the reduction of carbon by hydrogen to give methane ($CH_4$). Another relatively simple redox reaction is that between ethylene glycol and permanganate, as illustrated in FIG. 7. More complex redox reactions include the oxidation of sugars in the body via a series of electron transfer processes.

In some embodiments, the methods and systems provided herein can include a first thermochemical ablation reagent and a second thermochemical ablation reagent, wherein the first thermochemical ablation reagent comprises a reducing agent and the second thermochemical ablation reagent comprises an oxidizing agent. The particular combination of oxidizing and reducing agents can be selected to provide a suitable amount of heat with a relatively low level of reagents, and to result in innocuous byproducts with little or not toxicity to tissue in the vicinity of the targeted tissue. For example, the first thermochemical ablation reagent may comprise a reducing agent selected from the group consisting of, without limitation, glycerol, carbohydrates (e.g., dextrin, maltodextrin, glucose, sucrose), hydrogen peroxide ($H_2O_2$), iron(II) ammonium sulfate (($NH_4)_2Fe(SO_4)_2$), titanium trichloride ($TiCl_3$), cuprous chloride ($CuCl$), stannous sulfate ($SnSO_4$), and sodium thiosulphate ($Na_2S_2O_3$). The second thermochemical ablation reagent may comprise an oxidizing agent selected from the group consisting of, without limitation, permanganate ($MnO_4^-$), sodium hypochlorite ($NaOCl$), $H_2O_2$, iron (II) ammonium sulfate, and ammonium persulfate (($NH_4)_2S_2O_8$). In some cases, the reducing agent may be glycerol, glucose, or sucrose, and the oxidizing agent may be permanganate.

Thermite reactions also may be useful if the reagents are combined in appropriate concentrations and amounts, since such reactions can generate short bursts of very high temperatures focused on a very small area for a short period of time. Thermite fuels (reducing agents) include, for example, aluminium, magnesium, calcium, titanium, zinc, silicon, and boron. Such fuels can be oxidized by, e.g., boron(III) oxide, silicon(IV) oxide, chromium(III) oxide, manganese(IV) oxide, iron(III) oxide, iron(II,III) oxide, copper(II) oxide, and lead(II,II,IV). When aluminium is used, for example, it can reduce the oxide of another metal (e.g., iron oxide) in a redox reaction to give aluminium oxide, free elemental iron, and a large amount of heat:

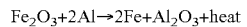

Other metal oxides (e.g., chromium oxide or copper) also can be used to generate elementary metal. For example, copper oxide and aluminium can be combined:

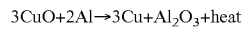

Those skilled in the art will appreciate that some oxidizing and reducing agents are not likely to be suitable for the methods and systems provided herein. For example, while nitric acid and ammonium nitrate are oxidizing agents, they are likely too powerful to be useful in an in vivo thermochemical ablation system. Further, thermite reactions may require a very high temperature (e.g., about 150° C.) to occur, such as when a compound such as perchlorate ($ClO_4$) is used as an oxidizing agent.

The oxidizing and reducing agents can be provided at any suitable concentrations, up to limits of solubility and/or availability (e.g., about 0.1 M, about 0.2 M, about 0.5 M, about 0.75 M, about 1 M, about 1.5 M, about 2 M, about 3 M, about 4 M, about 5 M, about 6 M, about 7 M, about 8 M, about 9 M, about 10 M, or any range therebetween, such as about 0.1 M to about 1 M, about 0.5 M to about 5 M, about 1 M to about 3 M, or about 1 M to about 10 M). Further, the oxidizing and reducing agents can be administered in any suitable amounts (e.g., about 100 µl, about 250 µl about 500 µl, about 750 µl, about 1 ml, about 2 ml, about 3 ml, about 4 ml,. about 5 ml, about 6 ml, about 7 ml, about 8 ml, about 9 ml, about 10 ml, or any range therebetween, such as about 100 µl to about 1 ml, about 500 µl to about 5 ml, or about 1 ml to about 10 ml). In some embodiments, oxidizing and reducing agents can be administered at a stoichiometry such that there will be little or no "leftover" reagents after the redox reaction has occurred. In other cases, the reagents can be administered in a ratio outside the usual stoichiometry. In such cases, there may be an excess of an acidic or basic reagent left over from the redox reaction, which may shift the pH at the target site. A pH shift can increase the sensitivity of cells at the target site to heat from the thermochemical redox reaction.

The reducing agent can be maintained separate from the oxidizing agent until the two agents reach the distal portion of the injection cannula where, as described below, they can be simultaneously infused into the targeted tissue, and can mix and chemically react with one another to generate the ablation heat energy. In some cases, oxidizing and/or reducing agents can react with compounds present in the tissue at or near the target site. For example, an agent such as permanganate can react with and reduce sugars present at a target site to thermochemically generate heat for ablation.

It should be understood from the description herein that, in some embodiments, the first and second thermochemical ablation reagents may include other reactive substances. For example, the first thermochemical ablation reagent may comprise useful imaging or other analyzable features (e.g., fluorescence, nuclear isotopes, MR imaging characteristics, or the like) to permit a health care professional to evaluate the reagent distribution in the targeted tissue and throughout the body.

In some embodiments, one or both of the oxidizing and reducing agents may be mixed with a denaturing agent that enhances the tissue ablation process. For example, a denaturing agent as described herein can be mixed with the oxidizing or reducing agent prior to injection to a tumor site. The denaturing agent may act upon the targeted tissue to enhance the ablation effects caused by the thermochemical reaction of the first and second reagents.

Moreover, in some embodiments, a drug may be added to one or both of the thermochemical ablation reagents so as to provide a pharmacological effect on the targeted tissue in addition to the thermochemical ablation effects. In one example, a chemotherapy drug can be added to a delivery device to mix with the first or second reagent prior to injection. The chemotherapy drug can be administered to the targeted tissue to provide pharmacological effects contemporaneously with the ablation effects from thermochemical reaction of the first and second reagents. In another example, an anesthetic (e.g., lidocaine or procaine) can be administered to the targeted tissue to assist with pain control.

2. Thermochemical Ablation Using Heat of Hydration

The methods and systems provided herein also may provide thermochemical heat from a hydration reaction. The heat of hydration for ions corresponds to the heat that is released by hydration of one mole of ions at a constant pressure. The more the ion is hydrated, the more heat is released. The degree of hydration depends on the size and charge of the ion - the smaller the ion and the greater its charge, the more hydrated it will become, producing more heat.

Thus, in some embodiments, a system can comprise a highly reactive thermochemical ablation reagent that, when it comes into contact with water present at the target tissue (or water that is added with the ablation reagent, e.g., via a dual chamber device as described herein), will undergo hydration, resulting in a release of heat. Chemical agents that can be used to generate heat of hydration include, without limitation, calcium oxide (CaO), which can be hydrated to calcium hydroxide ($Ca(OH)_2$)), and sulfuric acid ($H_2SO_4$). The hydration reaction of sulfuric acid is highly exothermic, and results in formation of sulfate and hydronium ions:

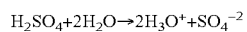

$$H_2SO_4 + 2H_2O \rightarrow 2H_3O^+ + SO_4^{-2}$$

Other useful reagents for hydration reactions include, without limitation, potassium hydroxide (KOH) and sodium hydroxide (NaOH), hydration of which is quite exothermic.

Those skilled in the art will appreciate that some reagents are not likely to be suitable for the methods and systems provided herein. For example, hydration of some reagents may be more powerful than would be useful in an in vivo thermochemical ablation system.

When administered in liquid form, the reagent to be hydrated can be provided at any suitable concentration, up to limits of solubility and/or availability (e.g., about 0.1 M, about 0.2 M, about 0.5 M, about 0.75 M, about 1 M, about 1.5 M, about 2 M, about 3 M, about 4 M, about 5 M, about 6 M, about 7 M, about 8 M, about 9 M, about 10 M, about 12 M, about 15 M, about 18M, about 20 M, or any range therebetween, such as about 0.1 M to about 1 M, about 0.5 M to about 5 M, about 1 M to about 10 M, or about 17 M to about 19 M). Further, the reagent can be administered in any suitable amount (e.g., about 100 µl, about 250 µl, about 500 µl, about 750 µl, about 1 ml, about 2 ml, about 3 ml, about 4 ml, about 5 ml, about 6 ml, about 7 ml, about 8 ml, about 9 ml, about 10 ml, or any range therebetween, such as about 100 µl to about 1 ml, about 500 µl to about 5 ml, or about 1 ml to about 10 ml).

In some embodiments, a reagent to be hydrated may be administered as a gel or a solid. For example, a solid piece of CaO (e.g., as a rod, a bead, or any other suitable form) can be implanted at a target site to be ablated. In addition, it is noted that in some cases, hydration can result in products (e.g., $Ca(OH)_2$) that may be therapeutically beneficial by, for example, sensitizing cells to the heat of hydration.

In some embodiments, a thermochemical ablation reagent to be hydrated may include other reactive substances. For example, an ablation reagent may comprise useful imaging or other analyzable features (e.g., fluorescence, nuclear isotopes, MR imaging characteristics, or the like) to permit a health care professional to evaluate the reagent distribution in the targeted tissue and throughout the body.

In some embodiments, a thermochemical ablation agent to be hydrated may be mixed with a denaturing agent that enhances the tissue ablation process. A denaturing agent as described herein can be mixed with the thermochemical ablation reagent to be hydrated prior to delivery to a tumor site.

The denaturing agent may act upon the targeted tissue to enhance the ablation effects caused by the thermochemical hydration reaction.

Moreover, in some embodiments, a drug may be added to a thermochemical ablation reagent to be hydrated, so as to provide a pharmacological effect on the targeted tissue in addition to the thermochemical ablation effects. In one example, a chemotherapy drug can be added to a delivery device to mix with the ablation reagent prior to injection. The chemotherapy drug can be administered to the targeted tissue to provide pharmacological effects contemporaneously with the ablation effects from thermochemical reaction of the hydrated reagent. In another example, an anesthetic (e.g., lidocaine or procaine) can be administered to the targeted tissue to assist with pain control.

3. Chemical Ablation Using Denaturants

In some embodiments, the methods and systems provided herein can result in ablation of target (e.g., tumor) tissue as a result of protein denaturation, which can lead to cell death. Such results can be achieved by, for example, delivering to a target site one or more chemicals such as, without limitation, urea, alcohols (e.g., methanol, ethanol, propanol, or isopropanol), surfactants, detergents, sclerosants, bifunctional reagents (e.g., formaldehyde or glutaraldehyde), guanidinium chloride, lithium perchlorate, sodium perchlorite (or another substance from the Hofmeister series), 2-mercaptoethanol, and dithiothreitol. In some cases, the use of a combination of denaturants (either sequentially or simultaneously) may be particularly useful, as each denaturant may be effective at lower concentrations than if they were used individually. For example, a combination of 250 mM urea and 2-3% ethanol may be useful to ablate tumor tissue, whereas greater concentrations of these agents may be needed if they are used singly.

Denaturants can be administered at any suitable concentrations, up to limits of solubility and/or availability (e.g., about 0.1 M, about 0.2 M, about 0.25 M, about 0.3 M, about 0.4 M, about 0.5 M, about 0.75 M, about 1 M, about 1.5 M, about 2 M, about 2.5 M, about 3 M, about 4 M, about 5 M, about 6 M, about 7 M, about 8 M, or any range therebetween, such as about 0.1 M to about 1 M, about 0.2 M to about 2 M, or about 0.25 M to about 0.5 M; or about 0.5%, about 0.75%, about 1%, about 2%, about 3%, about 4%, about 5%, or any range therebetween, such as about 0.5% to about 3%, or about 1% to about 2%). Further, the denaturants can be administered in any suitable amounts (e.g., about 100 about 250 µl, about 500 about 750 µl, about 1 ml, about 2 ml, about 3 ml, about 4 ml, about 5 ml, about 6 ml, about 7 ml, about 8 ml, about 9 ml, about 10 ml, about 20 ml, about 50 ml, about 100 ml, about 200 ml, about 250 ml, about 300 ml, about 350 ml, about 400 ml, about 500 ml, or any range therebetween, such as about 100 µl to about 1 ml, about 500 µl to about 5 ml, or about 1 ml to about 10 ml), or more than 500 ml.

Figure 5:
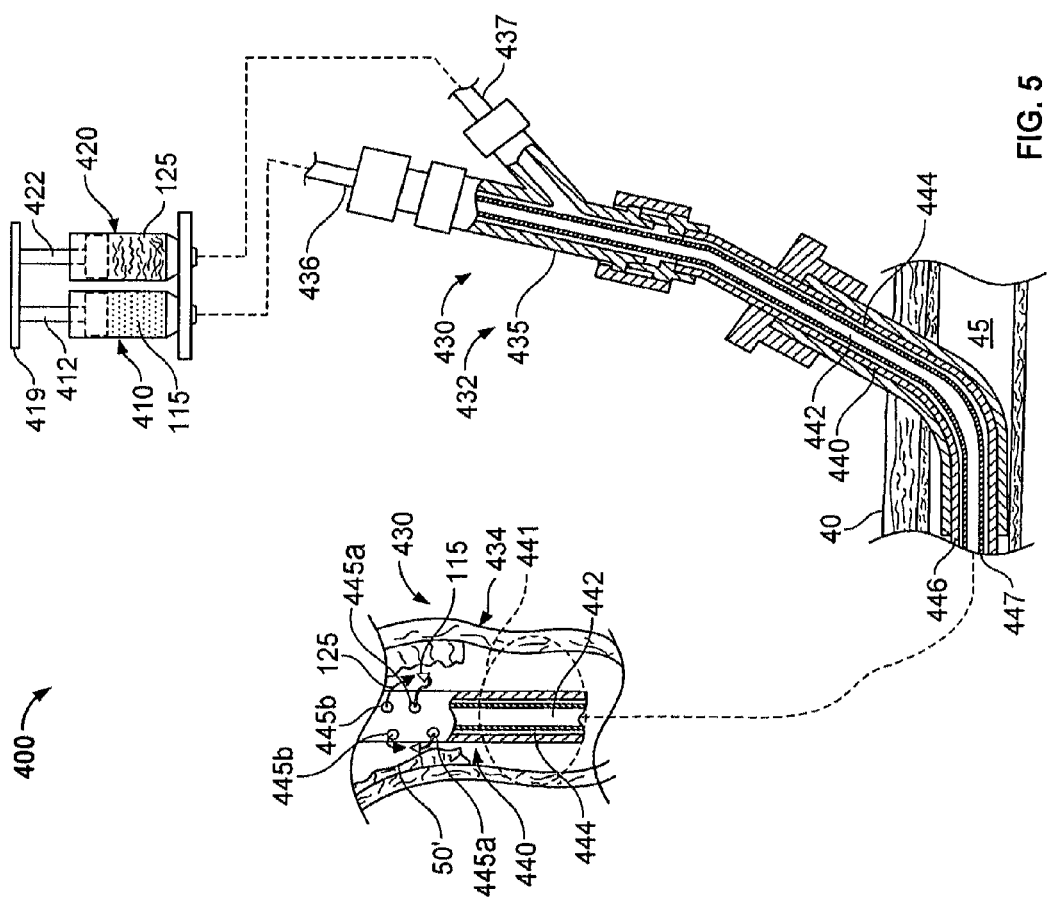
FIG. 5 is a section view of an alternative embodiment of a thermochemical ablation system.
Figure 6:
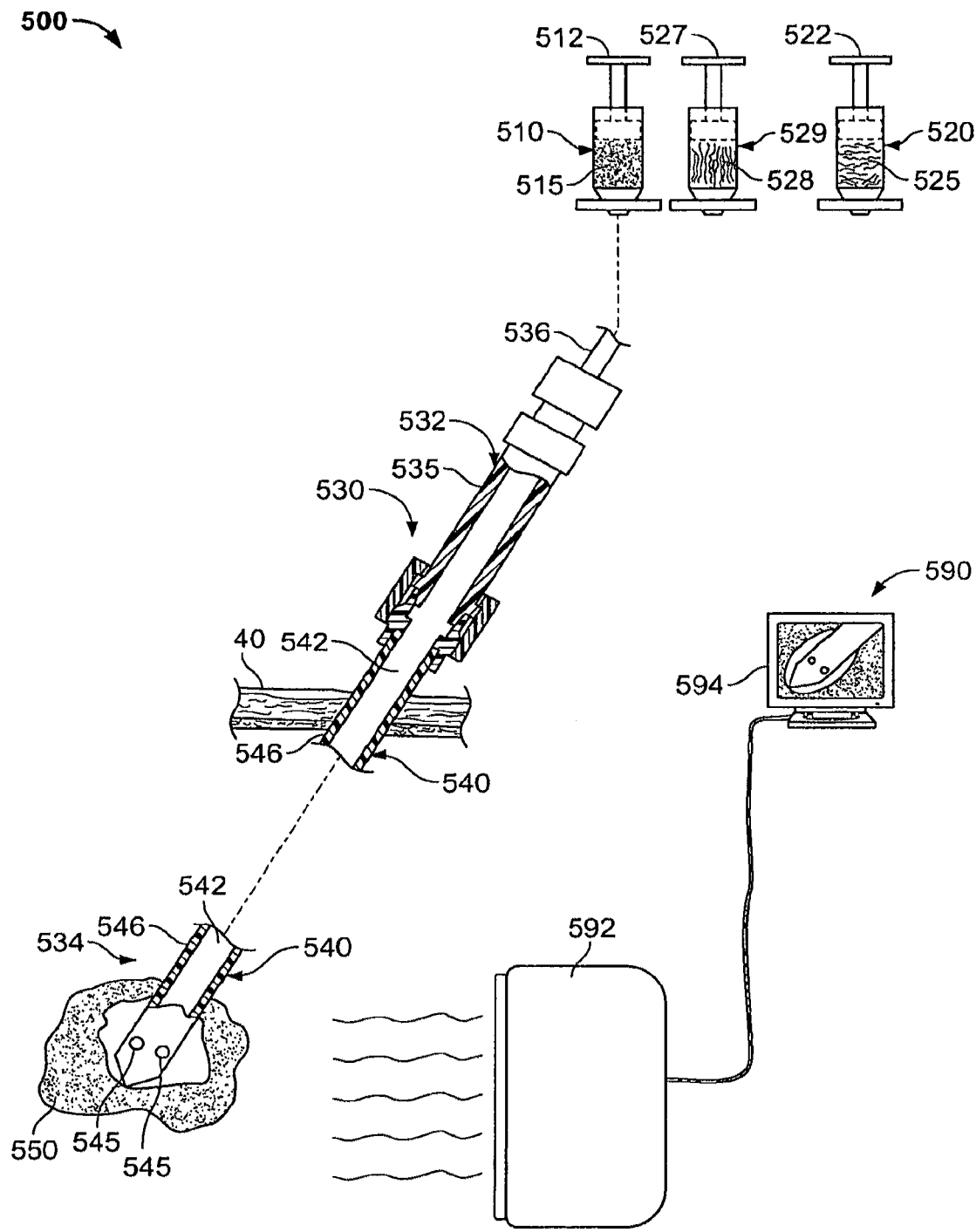
FIG. 6 is a section view of an alternative embodiment of a thermochemical ablation system.

Because there may be no reaction between denaturants given in combination (e.g., urea and ethanol), they can be combined prior to being taken up in a delivery means (e.g., a needle or catheter, or a device as depicted in FIG. 6. In some embodiments, it may be useful to administer a combination of denaturants using a dual chamber device as depicted in FIGS. 1-5, for example, so that the reagents are not combined until or just prior to deliver to the target site.

As described above, oxidizing and/or reducing agents, or reagents to be hydrated, may be mixed with a denaturing agent that enhances the tissue ablation process. For example, a denaturing agent as described herein can be mixed with an oxidizing or reducing agent or a reagent to be hydrated prior to delivery to a tumor site. In some cases, a site can be treated with one or more denaturants prior to treatment with redox reagents or a hydration reagent. The denaturing agent(s) may act on the targeted tissue to enhance the ablation effects caused by the thermochemical reaction of the other ablation reagents.

In some embodiments, a drug may be added to a denaturing agent so as to provide a pharmacological effect on the targeted tissue in addition to the chemical ablation effects. In one example, a chemotherapy drug can be added to a delivery device to mix with the ablation reagent prior to injection. The chemotherapy drug can be administered to the targeted tissue to provide pharmacological effects contemporaneously with the ablation effects from chemical action of the denaturing agent. In another example, an anesthetic (e.g., lidocaine or procaine) can be administered to the targeted tissue to assist with pain control.

4. Ablation Using a Dual Chamber System

Referring to FIG. 1, a thermochemical ablation system 100 is capable of infusing thermochemical ablation reagents into targeted tissue 50 to induce a chemical reaction and thereby ablate the tissue 50. The system 100 includes a first fluid reservoir 110 and a second fluid reservoir 120 that are in fluid communication with a thermochemical ablation device 130. The first reservoir 110 may include a first thermochemical ablation reagent 115 (such as a reducing agent, or a reagent to undergo hydration at the targeted tissue), and the second reservoir 120 may include a second thermochemical ablation reagent 125 (such as an oxidizing agent, or water/an aqueous solution for a hydration reaction). Also, each of the reservoirs 110 and 120 includes an actuator 112 and 122 that can be adjusted to provide a dispensing force to the reagents 115 and 125. Accordingly, the first and second reservoirs 110 and 120 can be actuated to deliver both reagents 115 and 125 to a proximal portion 132 of the fluid delivery device 130, which then passes the reagents 115 and 125 to a distal portion 134 of the device 130. In this embodiment, the first actuator 112 and the second actuator 122 are coupled to one another with a coupling 119 so that both actuators 112 and 122 can be simultaneous adjusted. For example, a user may apply a force to the coupling 119 to contemporaneously adjust the actuators 112 and 122, which causes the first and second reagents 115 and 125 to be simultaneously delivered to the device 130. In another example, a physician or other user may selectively activate a computer-controlled mechanism that acts upon the coupling 119 to provide the adjustment force. Such a computer-controlled mechanism may provide for accurate dosages of the reagents 115 and 125 delivered from the reservoirs 110 and 120. In other embodiments, the first and second reservoirs 110 and 120 may not be coupled to one another, and the actuators 112 and 122 may be separately adjusted to dispense the reagents simultaneously or in selected sequence.

In this embodiment, the thermochemical ablation device 130 includes a multi-lumen cannula 140 that can simultaneously infuse the first and second thermochemical ablation reagents 115 and 125 into the targeted tissue 50 proximate the distal portion 134. In particular, the cannula 140 includes a first lumen 142 in fluid communication with the first reservoir 110 to deliver the first thermochemical ablation reagent 115 to the distal portion 134. Also, the cannula 140 includes a second lumen 144 in fluid communication with the second reservoir 120 to deliver the first thermochemical ablation reagent 125 to the distal portion 134. The distal portion 134 of the cannula 140 may include a plurality of fluid ports 145a-b to radially disperse the first and second thermochemical ablation reagents 115 and 125 and thereby mix the reagents 115 and 125 in the region proximate the distal portion 134. It should be understood that, in other embodiments, three or more reservoirs may be used to deliver three or more thermochemical ablation reagents to the targeted tissue 50. In such circumstances, thermochemical ablation device may include a multi-lumen cannula having three or more lumens, each of which being in fluid communication with an associated fluid reservoir.

Still referring to FIG. 1, this embodiment of the fluid delivery device 130 includes a cannula 140 in the form of a percutaneous injection needle. For example, the cannula 140 may include a generally rigid needle body 146 having an outer diameter of about 0.135 inches or less, about 0.120 inches to about 0.008 inches, and about 0.072 inches to about 0.028 inches. The needle body 146 may comprise stainless steel or another generally rigid material that is suitable for percutaneous insertion through the patient's skin 40. Furthermore, the distal tip portion of the cannula 140 may include a pointed tip so as to facilitate penetration through the skin 40 and toward the targeted tissue 50. The cannula 140 may also include an internal tube 147 that passes through the needle body 146. In this embodiment, the internal tube 147 comprises a second, smaller needle body that is generally coaxial with the outer needle body 146, thereby defining the first lumen 142 within the second lumen 144. It should be understood that, in other embodiments, the first and second lumens 142 and 144 may be configured to have a side-by-side arrangement (refer, for example, to FIG. 3). In such circumstances, the first and second lumens 142 and 144 may be defined by two bores that are formed through the outer needle body 146 (e.g., without using a centrally located internal tube 147).

In some embodiments, the fluid delivery device 130 may be packaged as part of a thermochemical ablation kit, which the physician or other user can use without the need to further assemble any components of the device 130. For example, the fluid delivery device 130 may be manufactured so that outer needle body 146, the inner tube 147, and a valve device 135 are fully assembled and packaged into the kit. Also, the cannula 140 can be manufactured so that the first lumen 142 is in fluid communication with side ports 145*a* and the second lumen 144 is in fluid communication with the side ports 145*b* (described in more detail below, for example, in connection with FIGS. 2-4). In these circumstances, the physician or other user can readily unpackage the fluid delivery device 130 from the kit and thereafter connect both the first fluid line 136 of the fluid delivery device 130 to the first reservoir 110 and the second fluid line 137 to the second reservoir 120. Such fluid line connections permit the first and second reservoirs 110 and 120 to be in fluid communication with the first and second lumens 142 and 144.

As shown in FIG. 1, the distal portion 134 of the fluid delivery device 130 may include one or more side ports 145*a-b* through which the first and second reagents 115 and 125 are dispensed into the targeted tissue 50. The side ports 145*a-b* may be oriented so that the thermochemical ablation reagents 115 and 125 are radially dispersed from the distal portion 132. Such radial dispersion of the thermochemical ablation reagents may provide improved mixing of the reagents 115 and 125 upon exiting the fluid delivery device 130 (e.g., due to increased turbulence). Furthermore, the radial dispersion through the side ports 145*a-b* can more evenly distribute the heat generated by the mixing of the reagents 115 and 125.

The first set of side ports 145*a* may be in fluid communication with the first lumen 142 so that the first thermochemical ablation reagent 115 is evacuated from the side ports 145*a* when the coupler 119 (and first actuator 112) is adjusted. Likewise, the second set of side ports 145*b* may be in fluid communication with the second lumen 144 so that the second thermochemical ablation reagent 125 is evacuated from the side ports 145*b* when the coupler 119 (and second actuator 112) is adjusted. Accordingly, the fluid delivery device 130 provides for simultaneous infusion of the first and second reagents 115 and 125 into the targeted tissue 50, during which the thermochemical ablation reagents 115 and 125 mix with one another to cause an exothermic chemical reaction. If the first and second reagents 115 and 125 are to be infused in different proportions, the first reservoir 110 may have a different configurations (e.g., different cross-sectional areas) so that different amounts of fluid are dispensed when the actuators 112 and 122 are simultaneously adjusted (e.g., using the coupler 119). In some embodiments, the concentration of the base reagent or the acid reagent can be selected so as to fully neutralize the acid and base load applied to the targeted tissue 50 after the thermochemical ablation reaction. In other embodiments, the concentration of the base reagent or the acid reagent can be selected so as to partially neutralize the acid or base load while generating heat energy, thereby providing heated solution with a limited and safe level of remaining acid or base load.

The heat generated from this chemical reaction may be sufficient to ablate at least a portion of the targeted tissue 50 surrounding the distal portion 134 of the fluid delivery device 130. Because the fluid delivery device 130 infuses two reagents that chemically react with one another (rather than direct injection of a single acidic reagent), the byproducts of the chemical reaction may include greater heat generation with lower acid (or base) load toxicity. For example, in some embodiments, the fluid delivery device 130 can infuse both an acid reagent and a base reagent to create a larger lesion in the targeted tissue 50 (e.g., larger than would otherwise be obtained by direct injection acetic acid alone) while simultaneously reducing the acid load, whether by lesion expansion or by a thermal injury. Accordingly, the thermochemical ablation techniques described herein may be used to treat larger tumors in one or two sessions with fewer complications from acid (or base) load toxicity.

Still referring to FIG. 1, some embodiments of the thermochemical ablation system 100 may include a medical imaging system that provides real-time monitoring of the device 130 insertion and the delivery of the reagents 115 and 125. For example, the medical imaging system can include an ultrasound imaging system 190 to enable a physician or other user to view the distal portion 134 of the fluid delivery device 130 in the targeted tissue 50. In this embodiment, the ultrasound imaging system 190 includes an ultrasound probe device 192 that can be manipulated on the outside of the patient's body or within a body cavity. The ultrasound probe 192 may be connected to an ultrasound display system 194 that interprets the signals from the probe 192 and generates a display of the targeted portion of the patient's body. For example, as shown in FIG. 1, the ultrasound display system 194 may show the distal portion 134 of the device 130 as it is inserted into the targeted tissue 50 for delivery of the thermochemical ablation reagents 115 and 125. It should be understood that, in other embodiments, the imaging system may comprise another type of system other than the ultrasound imaging system 190. For example, the medical imaging system may include a CT imaging system or the like. Some or all of the delivery device 130 may comprise materials that are compatible with the selected imaging system so as to enable monitoring of the delivery device 130 during insertion. For example, the cannula 140 may comprise a metallic material that can be visualized using the ultrasound imaging system 190. In another example, the distal portion 134 of the delivery device 130 may include magnetic resonance markers or other features that permit viewability using the selected imaging system. Furthermore, in some embodiments, the delivery device 130 may include depth markers that are directly viewable to the physician or other user. For example, the cannula 140 may include a number of depth markers on the outer surface of the needle body 146. The physician or other user can view these depth markers during insertion of the cannula 140 through the skin 40 to indicate the approximate depth of insertion.

Figure 2:
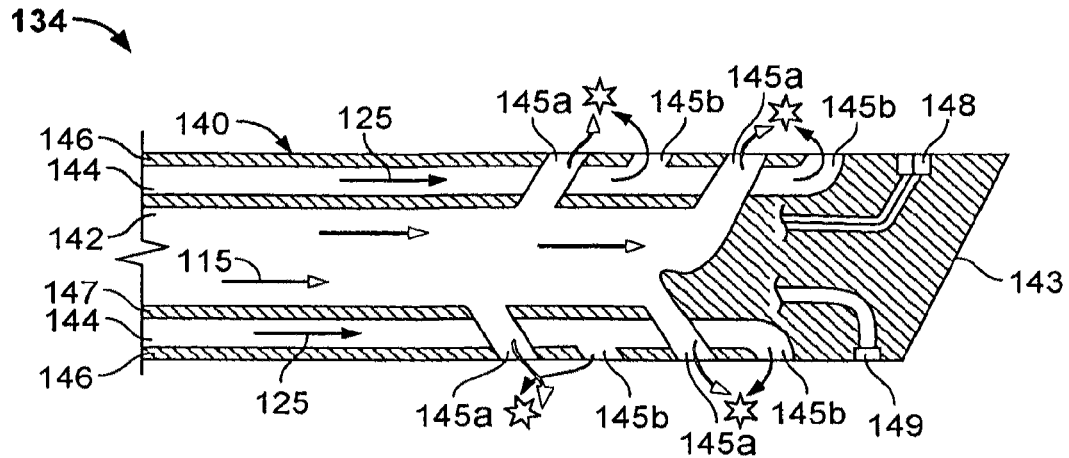
FIG. 2 is a cross-sectional view of a portion of a delivery cannula for a thermochemical ablation system, in accordance with some embodiments.

Referring to FIG. 2, the distal portion 134 of the fluid delivery device 130 may include one or more side ports 145a-b in the cannula 140. As previously described, the side ports 145a-b can be used to radially disperse the first and second thermochemical ablation reagents 115 and 125 and thereby mix the reagents 115 and 125 in the region proximate the distal portion 134. Such radial dispersion of the thermochemical ablation reagents can improve the mixing of the reagents 115 and 125 upon exiting cannula 140 (e.g., due to increased turbulence). The first and second lumens 142 and 144 maintain the reagents 115 and 125 separate from one another until they reach the distal portion 134 and are dispensed from the ports, after which the reagents are capable of generating an exothermic chemical reaction for ablating the targeted tissue. In such circumstances, the radial dispersion through the side ports 145a-b can more evenly distribute the heat generated by the mixing of the reagents 115 and 125.

Figure 3:
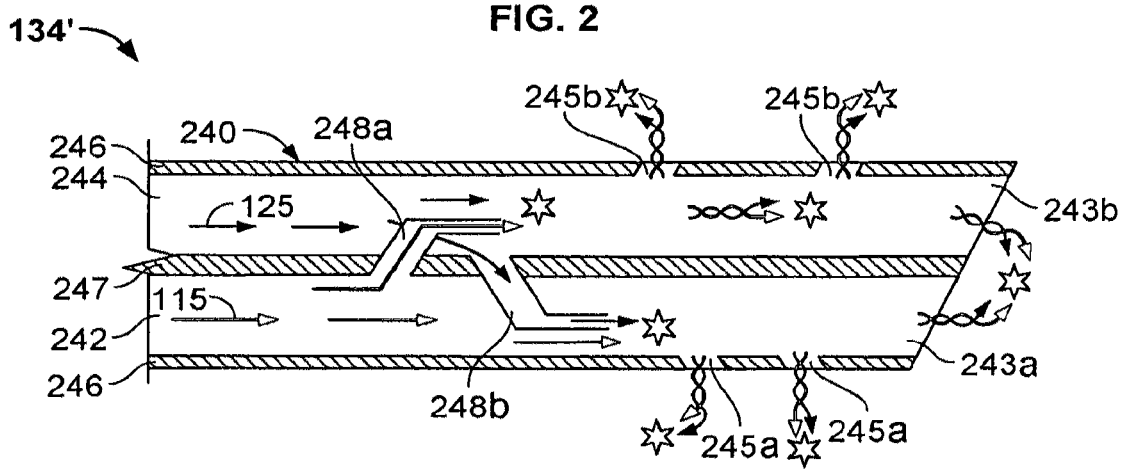
FIG. 3 is a cross-sectional view of a portion of an alternative delivery cannula for a thermochemical ablation system, in accordance with some embodiments.

It should be understood that, in some embodiments, the first and second thermochemical ablation reagents 115 and 125 may be at least partially mixed in the distal portion 134 immediately before being dispensed from the side ports 145a-b (refer, for example, to FIG. 3). Also, in other embodiments, the number of first side ports 145a and second side ports 145b may be different than that depicted in FIG. 2. For example, the cannula 140 may include only one first side port 145a and only one second side port 145b. In another example, the cannula 140 may include three, four, five, six, seven, eight, nine, ten, or more of the first side ports 145a. Also, the cannula 140 may include three, four, five, six, seven, eight, nine, ten, or more of the second side ports 145b. Furthermore, in some embodiments, the number of first side ports 145a may be different from the number of second side ports 145b. For example, the cannula 140 may include three of the first side ports 145a and four, five, or six of the second side ports 145b.

In this embodiment depicted in FIG. 2, the first lumen 142 is arranged coaxial with the second lumen 144. For example, the internal tube 147 may be disposed within the needle body 146 of the cannula 140 so as to define at least a portion of the first lumen 142 within the internal tube 147 and to define at least a portion of the second lumen 144 between the internal tube 147 and the needle body 146. The internal tube 147 may comprise a generally rigid material, such as stainless steel, a rigid polymer, or the like. Alternatively, the internal tube may comprise a non-metallic material (e.g., biocompatible polymer) that is assembled into the generally rigid needle body 146. It should be understood that, in other embodiments, the first and second lumens 142 and 144 may be arranged in the cannula 140 in a manner other than coaxial. For example, the first and second lumens 142 and 144 may be arranged in a side-by-side configuration (refer, for example, the embodiment described in connection with to FIG. 3).

Still referring to FIG. 2, the first lumen 142 is in fluid communication with the first set of side ports 145a such that the first thermochemical ablation agent 115 can be delivered through the first lumen 142 and out through the side ports 145a. Also, the second lumen 144 is in fluid communication with the second set of side ports 145b such that the second thermochemical ablation 125 agent can be delivered through the second lumen 144 and out through the side ports 145b. The walls that at least partially defines the first and second lumens (e.g., in this embodiment, the needle body 146 and the internal tube 147) are configured to maintain the reagents 115 and 125 separate from one another until they reach the distal portion 134 and are dispensed from the ports 145a-b. Upon dispensation from the side ports 145a-b, the thermochemical ablation reagents 115 and 125 can mix with one another to generate an exothermic chemical reaction—thereby using chemical reaction energy to ablate the targeted tissue.

In this embodiment, the cannula 140 includes a closed distal end 143. As such, the thermochemical ablation reagents 115 and 125 are dispensed from the side ports 145a-b rather than from end ports in the distal end 143. In some embodiments, the distal end may be formed with one or more end ports, and those end ports are plugged or otherwise sealed to ensure that the thermochemical ablation reagents 115 and 125 are dispensed only from the side ports 145a-b. As previously described, the side ports 145a-b can be used to radially disperse the first and second thermochemical ablation reagents 115 and 125, which can improve the mixing of the reagents 115 and 125 upon exiting cannula 140 (e.g., due to increased turbulence) and can more evenly distribute the heat generated by the mixing of the reagents 115 and 125.

Still referring to FIG. 2, some embodiments of the fluid delivery device 130 may include one or more sensors arranged on the distal portion 134. For example, in this embodiment, the distal portion 134 includes at least one temperature sensor 148 disposed at or near an outer surface of the cannula 140. The temperature sensor 148 may comprise a thermocouple instrument, such as a type K thermocouple, that has leads incorporated into the body of the cannula 140 (e.g., electrical lines embedded into the walls, insulated electrical traces formed on an inner or outer wall, or the like). The leads may extend from the temperature sensor 148 back to the proximal portion 132 (FIG. 1) of the fluid delivery device 130 so as to connect with a sensor computer system (not shown in FIGS. 1-2). The sensor computer system may be configured to indicate a temperature of the tissue disposed near the temperature sensor 148 based upon signals communicated from the temperature sensor 148. Such temperature information may be used, for example, by a physician or other user during the procedure to monitor the ablation of the targeted tissue.

In another example of a sensor, the distal portion 134 of the delivery device 130 may include at least one pH sensor 149 arranged disposed proximate an outer surface of the cannula 140. The temperature sensor 149 may comprise a pH probe instrument that has an electrical lead incorporated into the body of the cannula 140 (e.g., electrical lines embedded into the walls, insulated electrical traces formed on an inner or outer wall, or the like). The lead may extend from the pH sensor 149 back to the proximal portion 132 (FIG. 1) of the fluid delivery device 130 so as to connect with a sensor computer system (not shown in FIGS. 1-2). The sensor computer system may be configured to indicate a pH level of the material proximate the distal portion based upon signals communicated from the pH sensor 149. Such pH information may be used, for example, by a physician or other user during the procedure to monitor the acid load applied to the tissue during the delivery of the thermochemical ablation reagents 115 and 125. Other example of sensors that may be useful in the devices described herein include, for example, near infrared (NIR) sensors, Raman sensors, and the like.

Referring now to FIG. 3, some embodiments of the fluid delivery device may include a multi-lumen cannula in which at least one lumen is not arranged in a coaxial configuration.

In this embodiment, an alternative distal portion 134' of the fluid delivery device includes a cannula 240 having at least two lumens 242 and 244 in a non-coaxial configuration. The first lumen 242 is arranged adjacent to the second lumen 244. For example, the first and second lumens 242 and 244 may be at least partially defined by two adjacent bores form through the cannula 140. In such circumstances, the cannula 140 may comprise a generally rigid needle body 246 in which the first and second lumens 242 and 244 are formed and thereby separated by an intermediate wall portion 247.

Accordingly, the walls that at least partially define the lumens (e.g., in this embodiment, the needle body 246 and the intermediate wall portion 147) are configured to maintain the reagents 115 and 125 separate from one another until they reach the distal portion 134'. Thereafter, the first and second reagents 115 and 125 can at least partially mix (via internal ports 248a and 248b) before dispensing from the cannula 240. The first internal port 248a permits a portion of the first reagent 115 from the first lumen 242 to pass into the second lumen 244 in order to mix with a portion of the second reagent 125 in the distal portion 134'. Also, the second internal port 248b permits a portion of the second reagent 125 from the second lumen 244 to pass into the first lumen 242 in order to mix with a portion of the first reagent 115 in the distal portion 134'. In some circumstances, a portion of the first and second reagents 115 and 125 can mix with one another within the distal portion 134', and other portions of the first and second reagents 115 and 125 can mix after being dispensed from the ports of the distal portion 134'. By mixing at least a portion of the first and second thermochemical ablation reagents 115 and 125 in the distal portion 134' before dispensation into the targeted tissue, some portion of the dispensed fluid can be heated from the exothermic chemical reaction immediately before dispensation into the targeted tissue. It should be understood that, in other embodiments, the cannula 240 may not include the internal ports 248a-b so that the first and second reagents 115 and 125 do not mix within the distal portion 134 ' (e.g., mix after being dispensed from the distal portion 134').

Similar to previously described embodiments, the distal portion 134' may include one or more side ports 245a-b in the cannula 240 that can be used to radially disperse the first and second thermochemical ablation reagents 115 and 125. This radial dispersion of the thermochemical ablation reagents 115 and 125 can be used to mix at least a portion of the reagents 115 and 125 in the region proximate the distal portion 134' and that thereby generate an exothermic chemical reaction for ablating the targeted tissue. Further, the radial dispersion of the fluid from the side ports 245a-b can be used to more evenly distribute the heat energy from the exothermic chemical reaction. As shown in FIG. 3, a first set of side ports 245a extend from the first lumen 242, a second set of side ports 245b extend from the second lumen 244. The number of first side ports 245a and second side ports 245b may be different than that depicted in FIG. 3.

Still referring to FIG. 3, in this embodiment, the cannula 240 includes a distal end having end ports 243a and 243b. The first end port 243a extends from the first lumen 242 such that the first thermochemical ablation agent 115 (and the portion of the combined first and second reagent 115 and 125 mixed via the internal port 248b) can be delivered through the first lumen 242 and out through the first end port 243a. Also, the second end port 243b extends from the second lumen 244 such that the second thermochemical ablation agent 125 (and the portion of the combined first and second reagent 115 and 125 mixed via the internal port 248a) can be delivered through the second lumen 244 and out through the second end port 243b. Thus, the thermochemical ablation reagents 115 and 125 can be dispensed from the end ports 243a and 243b in addition to side ports 245a and 245b. When the unmixed portion of the first reagent 115 is delivered through the first end port 243a and the unmixed portion of the second reagent 125 is delivered from the second end port 243b, the unmixed portions of reagents 115 and 125 can subsequently mix and react with one another in a region distal of the cannula 240. In these circumstances, the physician or other user can manipulate the cannula 240 so as to delivery the thermochemical ablation energy to regions radially outward from the distal portion 134' and distally forward of the distal portion 134'. It should be understood that, in some embodiments, the cannula 240 having non-coaxial lumens 242 and 244 may include a closed distal end similar to that described in connection with FIG. 2.

In particular embodiments, the distal portion 134' of the fluid delivery device may include one or more sensors arranged on the cannula 240. For example, the cannula 240 may incorporate a temperature sensor (e.g., sensor 148 described in connection with FIG. 2), a pH sensor (e.g., sensor 149 described in connection with FIG. 2), or the like. Such sensors may provide useful information to the physician or other user during the ablation procedure.

In alternative embodiments, the cannula 240 may include end ports 243a-243b without any side ports 245a-b. In such embodiments, one or more end ports 243a may extend from the first lumen 242, and one or more end ports 243b may extend from the second lumen 244. The first and second thermochemical ablation reagents 115 and 125 would be delivered to the end ports 243a-b without an opportunity to pass through side ports 245a-b. Such a configuration may be used, for example, to ablate a specific and localized region of targeted tissue that is disposed generally distal of the tip of the cannula 240. It should be understood that, in these embodiments, the first and second lumens may be arranged in a coaxial configuration, in a side-by-side configuration, or a different configuration.

Figure 4:
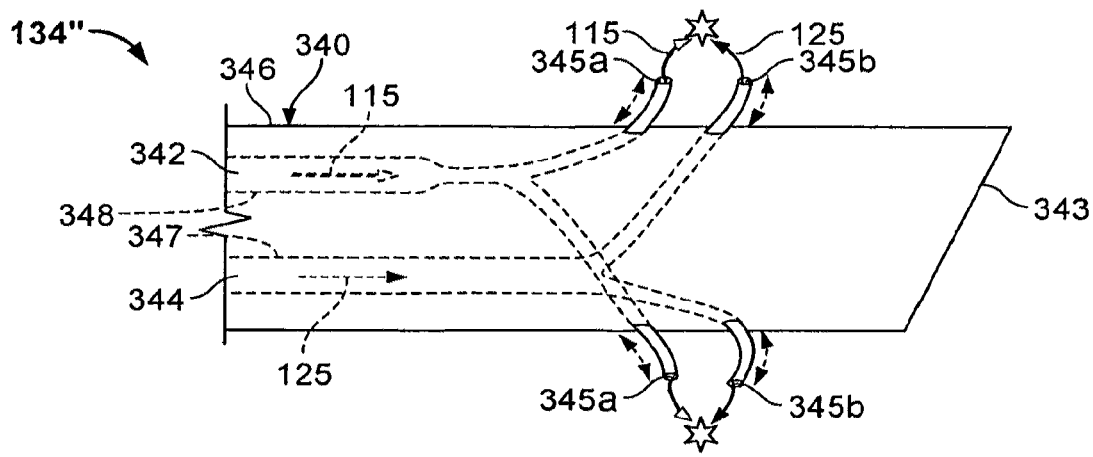
FIG. 4 is a cross-sectional view of a portion of yet another alternative delivery cannula for a thermochemical ablation system, in accordance with some embodiments.

Referring now to FIG. 4, some embodiments of the fluid delivery device may include a cannula with adjustable side projections that dispense the thermochemical ablation reagents 115 and 125. In this embodiment, an alternative distal portion 134" of the fluid delivery device includes a cannula 340 having at least two lumens 342 and 344 that can be adjusted relative to an outer needle body 346. For example, the first lumen 342 may be at least partially defined by a first tube 348 that can be actuated from a proximal position to a distal position so that first side projections 345 a protrude outwardly from the radial surface of the cannula 340. Similarly, the second lumen 344 may be at least partially defined by a second tube 347 that can be actuated from a proximal position to a distal position so that second side projections 345b protrude outwardly from the radial surface of the cannula 340. The first and second side projections 345a-b may include ports therein that dispense the first and second thermochemical ablation reagents 115 and 125 from the projections. Accordingly, the first and second side projections 345a-b can be adjusted from a retracted position (e.g., a position generally within a bore of the outer needle body 346) to an extended position (e.g., refer to FIG. 4) so as to penetrate into a wider region of the targeted tissue and further distribute the thermochemical ablation energy during delivery of the reagents 115 and 125.

In this embodiment, the outer needle body 346 comprises a generally rigid material (e.g., stainless steel or the like) and the first and second tubes 348 and 347 comprise a shape memory alloy that exhibits superelastic characteristics when inside the patient's body. For example, the first and second tubes 348 and 347 may comprise nitinol material or the like, which provides superelastic flexibility during the transition from the retracted position (e.g., the side projections 345*a-b* are constrained generally within a bore of the outer needle body 346) to the extended position (e.g., refer to FIG. 4). As such, the side projections 345*a-b* may have a curved shape or other configured that permits the ports of the side projections to be pointed toward particular regions.

In use, a physician or other user can direct the distal portion 134" to the targeted tissue under guidance from a medical imaging system 190 (FIG. 1). In such circumstances, the side projections 345*a-b* may be in the retracted position to facilitate insertion of the cannula 340 into the patient. When the targeted tissue is reached by the distal portion 134", the physician or other user may operate a trigger device or other actuator (not shown in FIG. 4) that causes the first and second tubes 348 and 347 to shift positions relative to the outer needle body 346. For example, the trigger device may cause the first and second tubes 348 and 347 to adjust distally, thereby forcing the side projections 345*a-b* to the extended position radially outward of the cannula 340. As such, the side projections 345*a-b* act as tines that penetrate into a wider region of the targeted tissue. Thereafter, the physician or other user can adjust the coupler 119 (FIG. 1) or other device so that the first and second thermochemical ablation reagents 115 and 125 are dispensed out of the ports in the side projections 345*a-b*. Upon release from the ports, the first and second thermochemical ablation reagents 115 and 125 are mixed with one another in a chemical reaction that generates heat to ablate the targeted tissue.

It should be understood that, in some embodiments, the cannula 340 may have lumens 342 and 344 that are arranged in a coaxial configuration, in a side-by-side configuration, or in a different configuration. In alternative embodiments, the first and second thermochemical ablation reagents 115 and 125 may be at least partially mixed in the distal portion 134" immediately before being dispensed from the ports of the side projections 345*a-b* (e.g., similar to embodiments described in connection with FIG. 3). Also, in some embodiments, the cannula 340 may have a number of side ports to dispense the first and second reagents directly from the cannula 340 (in addition to the fluid delivery from the side projections 345*a-b*). Further, in some embodiments, the cannula 340 may have a closed distal end similar to that described in connection with FIG. 2 or end ports similar to those described in connection with FIG. 3. In particular embodiments, the distal portion 134" of the fluid delivery device may include one or more sensors arranged on the cannula 340. For example, the cannula 340 may incorporate a temperature sensor (e.g., sensor 148 described in connection with FIG. 2), a pH sensor (e.g., sensor 149 described in connection with FIG. 2), or the like. Such sensors may provide useful information to the physician or other user during the ablation procedure.

Referring now to FIG. 5, some embodiments of a thermochemical ablation system 400 may include a fluid delivery device 430 having a cannula 440 that is at least partially flexible. For example, the cannula 440 may comprise a flexible catheter body 446 that is deliverable through a bodily passageway 45, including a vein, an artery, a urethra, a rectum, a vagina, an esophagus, or the like. Accordingly, a physician or other user can direct a distal portion 434 of the fluid delivery device 430 through the bodily passageway 45 and toward a targeted tissue 50' (e.g., a tumor, a vasculature occlusion such as varicoceles or varicose veins, a ureteral occlusion, or the like) for ablation or other treatment of the targeted tissue 50'.

Similar to previously described embodiments, the thermochemical ablation system 400 includes a first fluid reservoir 410 and a second fluid reservoir 420 that are in fluid communication with the thermochemical ablation device 430. The first reservoir 410 includes the first thermochemical ablation reagent 115, and the second reservoir 420 includes the second thermochemical ablation reagent 125. Each of the reservoirs 410 and 420 includes an actuator 412 and 422 that can be adjusted to provide a dispensing force to the reagents 115 and 125. The first actuator 412 and the second actuator 422 can be mechanically coupled to one another with a coupling 419 so that both actuators 412 and 422 can be simultaneous adjusted.

Similar to previously described embodiments, the cannula 340 of the fluid delivery device 430 includes a first lumen 442 in fluid communication with the first reservoir 410 and a second lumen 444 in fluid communication with the second reservoir 420. Also, the distal portion 434 of the delivery device 430 may include a plurality of fluid ports 445*a-b* to disperse the first and second thermochemical ablation reagents 115 and 125 and thereby mix the reagents 115 and 125 in the region proximate the distal portion 434.

Still referring to FIG. 5, this embodiment of the fluid delivery device 430 includes the cannula 440 in the form of a flexible catheter device. For example, the cannula 440 may includes a generally flexible catheter body 446 comprised of a biocompatible polymer. The fluid delivery device 430 may include a steering mechanism (e.g., steering wires, shape memory actuators, or the like) so that the distal tip of the cannula 440 can be navigated through the bodily passageway 45. The cannula 440 may also include an internal tube 447 that is formed inside the catheter body 446. As such, the first lumen 442 is at least partially defined by the internal tube 447, and the second lumen 444 is at least partially defined between the catheter body 446 and the internal tube 447. Thus, in this embodiment, the first and second lumens 442 and 444 are arranged in a coaxial configuration. In other embodiments, the first and second lumens 442 and 444 can be arranged in a side-by-side configuration or in other configurations.

The distal portion 434 of the fluid delivery device 430 may include one or more side ports 445*a-b* through which the first and second reagents 115 and 125 are dispensed into the targeted tissue 50'. The side ports 445*a-b* may be oriented so that the thermochemical ablation reagents 115 and 125 are radially dispersed from the distal portion 432. Such radial dispersion of the thermochemical ablation reagents may provide improved mixing of the reagents 115 and 125 upon exiting the fluid delivery device 430 (e.g., due to increased turbulence). Furthermore, the radial dispersion through the side ports 445*a-b* can more evenly distribute the heat generated by the mixing of the reagents 115 and 125. It should be understood that, in some embodiments, the cannula 440 may have a closed distal end similar to that described in connection with FIG. 2 or end ports similar to those described in connection with FIG. 3. Also, in alternative embodiments, the cannula 440 may include end ports without any side ports 445*a-b*. In particular embodiments, the distal portion 434 of the fluid delivery device 430 may include one or more sensors arranged on the cannula 440. For example, the cannula 440 may incorporate a temperature sensor (e.g., sensor 148 described in connection with FIG. 2), a pH sensor (e.g., sensor 149 described in connection with FIG. 2), or the like. Such sensors may provide useful information to the physician or other user during the ablation procedure.

As shown in FIG. 5, the first set of side ports 445*a* may be in fluid communication with the first lumen 442 so that the first thermochemical ablation reagent 115 is evacuated from the side ports 445*a* when the coupler 419 (and first actuator 412) is adjusted. Likewise, the second set of side ports 445b may be in fluid communication with the second lumen 444 so that the second thermochemical ablation reagent 125 is evacuated from the side ports 445 b when the coupler 419 (and second actuator 412) is adjusted. Accordingly, the fluid delivery device 430 provides for simultaneous infusion of the first and second reagents 115 and 125 into the targeted tissue 50', during which the thermochemical ablation reagents 115 and 125 mix with one another to cause an exothermic chemical reaction. The heat generated from this chemical reaction may be sufficient to ablate at least a portion of the targeted tissue 50' surrounding the distal portion 434 of the fluid delivery device 430. As previously described, the byproducts of the chemical reaction may include greater heat generation with lower acid (or base) load toxicity because the fluid delivery device 430 infuses two reagents that chemically react with one another (rather than direct injection of a single acidic reagent). It should be understood that, in some embodiments, the first and second thermochemical ablation reagents 115 and 125 may be at least partially mixed (via internal ports) in the distal portion 434 immediately before being dispensed from the side ports 445a-b (as described, for example, in connection with FIG. 3).

Still referring to FIG. 5, the fluid delivery device 430 may optionally include an expandable balloon device 441 disposed along the distal portion 434. The expandable balloon device 441 may be used to anchor the distal tip of the cannula 340 in a desired location with the bodily passage way 45. Alternatively, the expandable balloon may be used to temporarily seal the bodily passageway 45 during the delivery of the thermochemical ablation reagents 115 and 125 from the catheter body 446. For example, the balloon 441 may be filled in saline or another fluid to press against the wall of a vein or artery, thereby temporarily hindering blood flow through that portion of the vein or artery. The thermochemical ablation reagents 115 and 125 can be dispensed as previously described while the balloon 441 is expanded, which permits the reagents 115 125 to mix with one another in proximity to the targeted tissue and without being carried away by ordinary blood flow. After the ablation procedure is completed, the balloon may be collapse for removably of the fluid delivery device 430.

Some embodiments of the thermochemical ablation system 400 may include a medical imaging system that provides real-time monitoring of the device 430 insertion and the delivery of the reagents 115 and 125. For example, the medical imaging system can include an ultrasound imaging system 190 (refer, for example, to FIG. 1) to enable a physician or other user to view the distal portion 434 of the fluid delivery device 430 in the targeted tissue 50'. In another example, the medical imaging system may include a CT imaging system or the like. The delivery device 430 may comprise one or more materials that are compatible with the selected imaging system so as to enable monitoring of the delivery device 430 during insertion. For example, the cannula 440 may comprise a metallic material that can be visualized using the ultrasound imaging system 190. In another example, the catheter body 446 of the cannula 440 may include magnetic resonance markers inserted therein which provide viewability using the selected imaging system. Furthermore, in some embodiments, the delivery device 430 may include depth markers that are directly viewable to the physician or other user. For example, the outer catheter body 446 may include a number of depth markers. The physician or other user can view these depth markers during insertion of the cannula 140 through the skin 40 to indicate the approximate depth of insertion. Accordingly, a physician or other user can direct a distal portion 434 of the fluid delivery device 430 through the bodily passageway 45 and toward a targeted tissue 50' (e.g., a tumor, a vasculature occlusion such as varicoceles or varicose veins, a ureteral occlusion, or the like) for ablation or other treatment of the targeted tissue 50'.

5. Ablation Using a Single Chamber System

A chemical ablation system induce protein denaturation and apoptosis by dispensing one or more reagents at a target treatment location. For example, a combination of urea and ethanol can be administered to a tumor site to kill tumor cells. Such a combination of reagents can be mixed prior to administration (e.g., in a chamber of the delivery device) or at the targeted tissue, as described above. When the reagents are administered through separate chambers of a delivery device and mixed at the target site, a device as described above and shown in FIGS. 1-5 may be used. When the reagents are mixed prior to administration (e.g., in the delivery device), they can be injected or infused into the target using standard needles or catheters, for example. In some embodiments, a delivery system as shown in FIG. 6 can be used to deliver a combination of denaturing reagents. Such a system also can be used to deliver a reagent to be hydrated by water that is present in the body at the target site, for example.

Referring to FIG. 6, a thermochemical ablation system 500 is capable of infusing one or more reagents into targeted tissue 550 to ablate the tissue 550. The system 500 includes a fluid reservoir 510 that is in fluid communication with a chemical ablation device 530. The reservoir 510 may be detachable from the chemical ablation device 530. The reservoir 510 includes a reagent 515. The reservoir 510 includes an actuator 512 that can be adjusted to provide a dispensing force to the reagent 515. Accordingly, the reservoir 510 can be attached to the proximal end of the device 530 and actuated to deliver reagent 515 to a proximal portion 532 of the fluid delivery device 530, which then passes the reagent to a distal portion 534 of the device 530. In one approach, a user may manually apply a force to the reservoir 510 to deliver the reagent 515 to the device 530, or, in another approach, a physician or other user may selectively activate a computer-controlled mechanism that acts upon the reservoir 510 to provide the actuating force. A computer-controlled mechanism may provide for accuracy in small doses, may provide for using a dosage profile, or other effects for dosages of the reagent 515 delivered from the reservoir 510.

In one embodiment, the chemical ablation device 530 includes a cannula 540 that includes lumen 542 in fluid communication with the reservoir 510 to deliver the reagent 515 to the distal portion 534. The distal portion 534 of the cannula 540 may include a plurality of fluid ports 545 a-b to radially disperse the reagent 515 into the treatment location 550 proximate the distal portion 534.

Still referring to FIG. 6, this embodiment of the fluid delivery device 530 includes a cannula 540 in the form of a percutaneous injection needle. For example, the cannula 540 may includes a generally rigid needle body 546 having an outer diameter of about 0.135 inches or less, about 0.120 inches to about 0.008 inches, and about 0.072 inches to about 0.028 inches. The needle body 546 may comprise stainless steel or another generally rigid material that is suitable for percutaneous insertion through the patient's skin 40. In other embodiment, the needle may comprise a rigid plastic or ceramic material, or other metal such as titanium. The use of such materials may allow for real-time imaging using MRI or other imaging systems. Furthermore, the distal tip portion of the cannula 540 may include a pointed tip so as to facilitate penetration through the skin 540 and toward the targeted tissue treatment location 550.

In some embodiments, the fluid delivery device 530 may be packaged as part of a chemical ablation kit, which the physician or other user can use without the need to further assemble any components of the device 530. In these circumstances, the physician or other user can readily unpackage the fluid delivery device 530 from the kit and thereafter connect the first fluid line 536 of the fluid delivery device 530 to the reservoir 510.

As shown in FIG. 6, the distal portion 534 of the fluid delivery device 530 may include one or more side ports 545a-d through which the reagent 515 is dispensed into the targeted tissue treatment location 550. Such radial dispersion of the reagents may provide improved treatment of the target location by improved reagent distribution. Furthermore, the radial dispersion through the side ports can provide better localization of the reagent as the reagent is dispersed radially, compared to injecting as a single axial stream.

Dispensing of the reagent 515 at the target treatment location 550 can cause denaturation of proteins at the site being treated, and cell death (e.g., via apoptosis) can occur. The local denaturation caused by the reagent 515 may be sufficient to ablate at least a portion of the targeted tissue 550 surrounding the distal portion 534 of the fluid delivery device 530.

The reagent 515 that is infused into the targeted tissue 550 may be selected to provide a suitable energy deposition in tissue while providing a relatively low level of reaction byproducts and/or providing byproducts that are not harmful to the tissue surrounding or remote from the target site. For example, the reagent 515 may comprise a combination of urea and ethanol as discussed above. The reagent may also be selected to have useful imaging or other analyzable features (e.g., fluorescence, nuclear isotopes, MR imaging characteristics, or the like) to permit a physician or other user to evaluate the reagent distribution in the targeted tissue 550.

Still referring to FIG. 6, some embodiments of the chemical ablation system 500 may include a medical imaging system that provides real-time monitoring of the device 530 insertion and the delivery of the reagent 515. For example, the medical imaging system may include an ultrasound imaging system 590 to enable a physician or other user to view the distal portion 534 of the fluid delivery device 530 in the targeted tissue 550. In this embodiment, the ultrasound imaging system 590 includes an ultrasound probe device 592 that can be manipulated on the outside of the patient's body or within a body cavity. The ultrasound probe 592 may be connected to an ultrasound display system 594 that interprets the signals from the probe 592 and generates a display of the targeted portion of the patient's body. For example, the ultrasound display system 594 may show the distal portion 534 of the device 530 as it is inserted into the targeted tissue 550. It should be understood that, in other embodiments, the imaging system may comprise another type of system other than the ultrasound imaging system 590. For example, the medical imaging system may include a CT imaging system, MRI imaging system, or the like. Some or the entire delivery device 530 may comprise materials that are compatible with the selected imaging system so as to enable monitoring of the delivery device 530 during insertion. For example, the cannula 540 may comprise a metallic material that can be visualized using the ultrasound imaging system 590. In another example, the distal portion 534 of the delivery device 530 may include magnetic resonance markers or other features that permit viewability using the selected imaging system. Furthermore, in some embodiments, the delivery device 530 may include depth markers that are directly viewable to the physician or other user. For example, the cannula 540 may include a number of depth markers on the outer surface of the needle body 546. The physician or other user can view these depth markers during insertion of the cannula 540 through the skin 40 to indicate the approximate depth of insertion.

The system 500 may optionally include additional reservoirs that may be removably attached to the delivery device 530. For example, a second fluid reservoir 520 may be placed in fluid communication with the delivery device 530. The reservoir 520 includes a second reagent 525. The reagent 525 may be dispensed by activating actuator 522. In some embodiments, an inert reagent reservoir 529 may be placed in fluid communication with the delivery device 530. The reservoir 529 includes an inert reagent 528. The inert reagent 528 may be dispensed by activating actuator 527. The inert reagent may be used to, for example, improve the dispersion of reagents, improve visualization, or provide other beneficial effects.

The invention will be further described in the following examples, which do not limit the scope of the invention described in the claims.

EXAMPLES

Example 1

Heat for Thermochemical Ablation Based on Redox Chemistry

1. Materials and Methods

In vitro studies: All reagents were obtained from Sigma-Aldrich Chemical Co. (St. Louis, Mo.) unless otherwise noted. Sodium permanganate solutions of predetermined molarities were prepared by dissolving sodium permanganate monohydrate crystals in distilled water. Sodium permanganate solution and glycerol were then injected in triplicate into a clean 10 mL beaker using one of three different injection orders:

(1) Simultaneous injection using a coaxial injection device.
(2) Glycerol injection first, followed by sodium permanganate injection using a separate syringe (hereafter referred to as 'glycerol-first' injections).
(3) Sodium permanganate injection first, followed by glycerol injection using a separate syringe (hereafter referred to as 'permanganate-first' injections).

Figure 8:
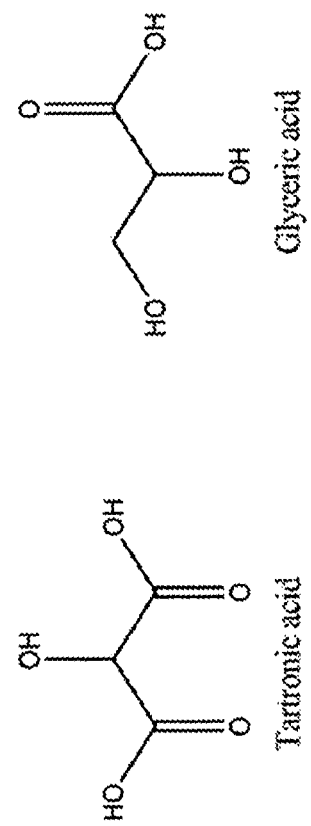
FIG. 8 is a diagram showing two of the oxidation products of the reaction between glycerol and permanganate.
Figure 9:
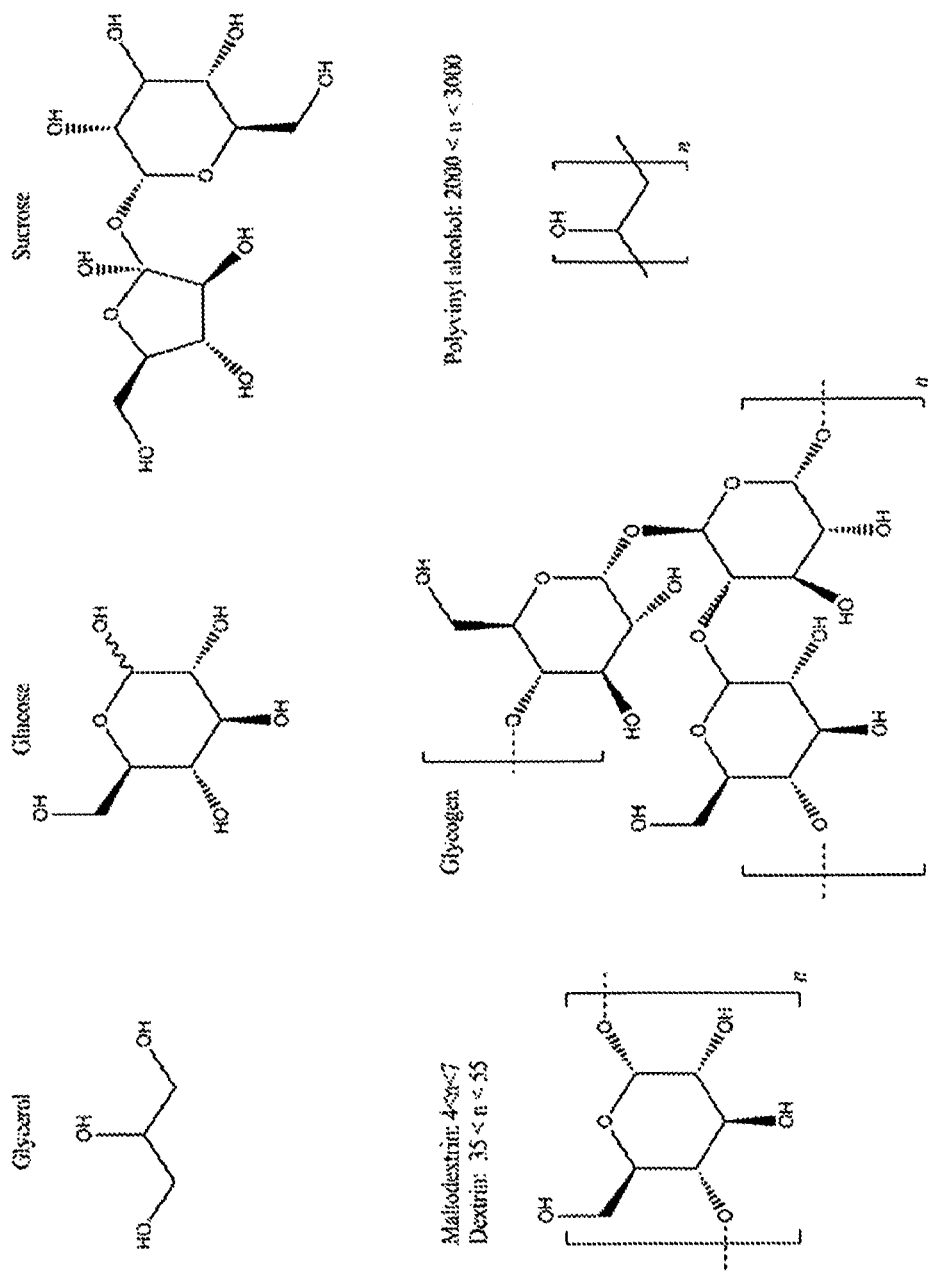
FIG. 9 is a diagram showing the structures and the increasing molecular complexity of the substrates used in the experiments described herein.

Exemplary reaction products of glycerol oxidation by permanganate include tartronic acid and glyceric acid (FIG. 8). Reaction temperature was measured by a thermocouple probe (type T MT-29/1; Physitemp Instruments, Clifton, N.J.) placed at the center of the beaker, with the tip submerged underneath the surface of the mixed solutions. Temperature recordings were made by a T-type thermocouple thermometer (Digi-Sense; Cole-Parmer, Vernon Hills, Ill.) at time intervals of 1 to 3 seconds from the onset of injections until the temperature dropped below 40° C. A series of different permanganate volumes (1, 2, and 3 mL) and concentrations (1 and 2M) were tested in order to study the effects of volume and concentration on temperature. Selected experiments were repeated with glucose, sucrose, maltodextrin (4-7 glucose unit average), and dextrin as substrates. The remaining substrates were different polysaccharides (starch, cellulose and glycogen) and polyvinyl alcohol. See, FIG. 9. All were used as 180 g/L (carbohydrates based on glucose) solutions and/or suspensions rather than expressing concentration in molarity due to their polymeric nature.

Ex vivo studies: As a proof of concept, ex vivo experiments were done by performing simultaneous injections of 1M glycerol and 2M permanganate at 0.5 or 1 mL each into porcine muscle tissue. The temperature was recorded using a thermocouple probe placed as closely as possible to the needle tip. After completion of injections, the tissues were sectioned and lesions were examined and imaged. An infrared camera (IRI4010; IRISYS Northampton, United Kingdom) also was used as an alternative method for assessing the temperature and the zone of thermal excursion at the lesion site by sectioning the tissue after completion of an injection.

2. Glycerol vs. Permanganate

Figure 10:
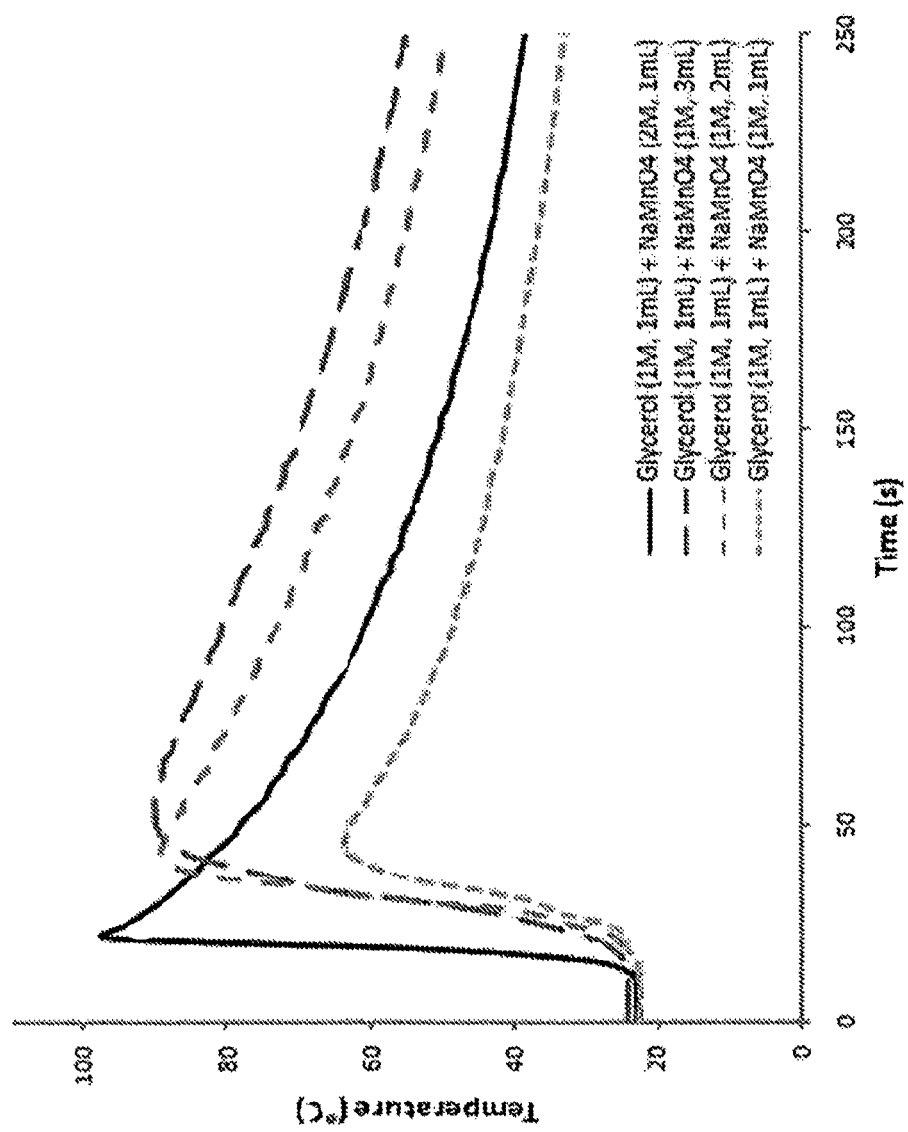
FIG. 10 is a graph plotting in vitro temperature profiles for simultaneous injection of the indicated amounts and concentrations of glycerol and permanganate.

Using 1M glycerol (1 mL) and 1M permanganate (1 mL), the average maximum temperatures recorded for simultaneous injections, glycerol-first injections, and permanganate-first injections were 63.9, 71.1, and 59.3° C. respectively. When the volume of the permanganate solution was raised to 2 mL, the average maximum temperatures for simultaneous, glycerol-first, and permanganate-first injections rose to 89.1, 86.7, and 70.3° C. respectively. Using 3 mL of permanganate solution, the average maximum temperatures for simultaneous, glycerol-first, and permanganate-first injections were 90.6, 90.3, and 77.9° C. respectively. Further increasing the volume of permanganate solution led to a decline in maximum temperatures. When the volume of glycerol was raised to 2 mL, a lower average maximum temperature was obtained for all three injection orders (53.1, 56.7, 54.1° C.). When the concentration of the permanganate solution was raised to 2 M, the average maximum temperatures for simultaneous, glycerol-first, and permanganate-first injections were 97.4, 99.1, and 97.0° C. respectively. Using 3 M permanganate solution (1 mL), the reaction mixture erupted and thus temperature recording was deemed unreliable under the circumstances. Averaged recordings for simultaneous injections of permanganate and glycerol under various conditions are depicted in FIG. 10.

Figure 11:
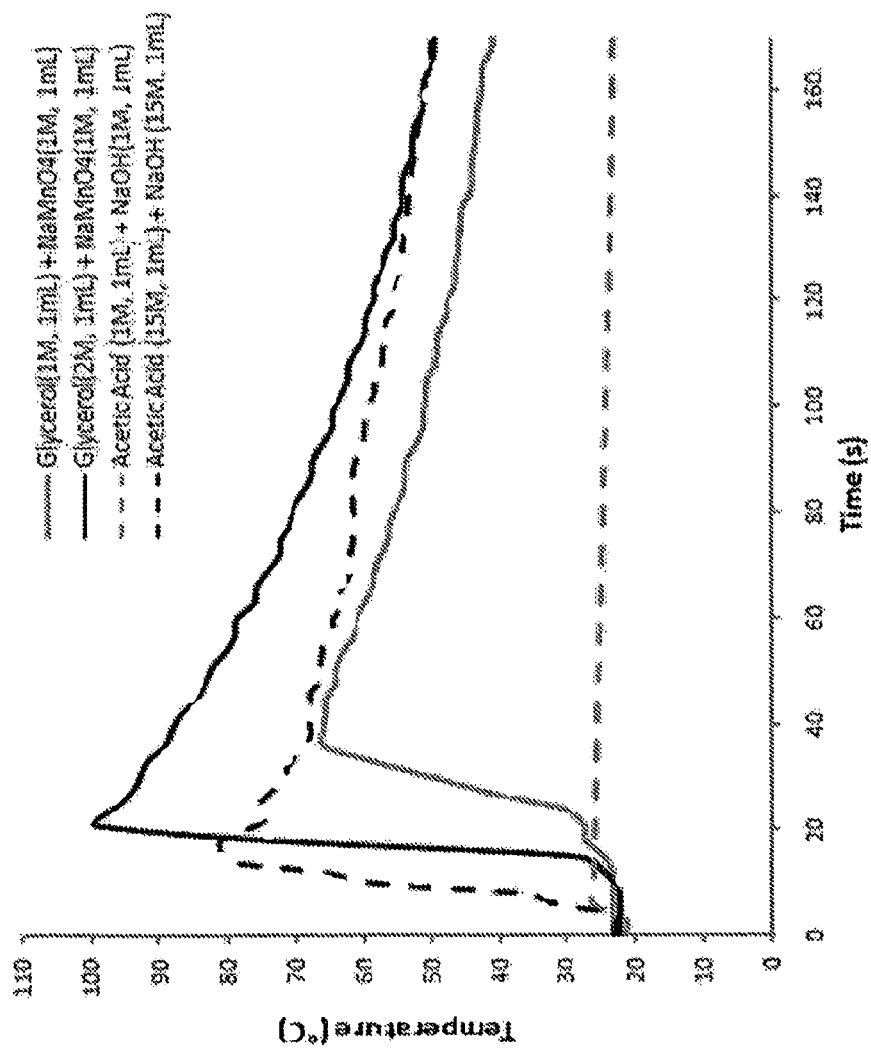
FIG. 11 is a graph plotting in vitro temperature profiles for simultaneous injection of the indicated amounts and concentrations of glycerol and permanganate or acetic acid and sodium hydroxide.

Further in vitro studies were conducted to compare redox and neutralization chemistries. As shown in FIG. 11, a permanganate/glycerol redox system was highly exothermic at a lower concentration than an acetic acid/sodium hydroxide neutralization system. In particular, permanganate was more efficient than acid/base neutralization in the sense that a low-molarity permanganate solution was capable of achieving a high maximum temperature (above 80° C.) that was produced by an equivalent volume of acid and base at a much higher molarity. Another potential advantage of using a permanganate redox system is the flexibility to manipulate reaction kinetics by using different substrates.

3. Glucose vs. Permanganate

Figure 12:
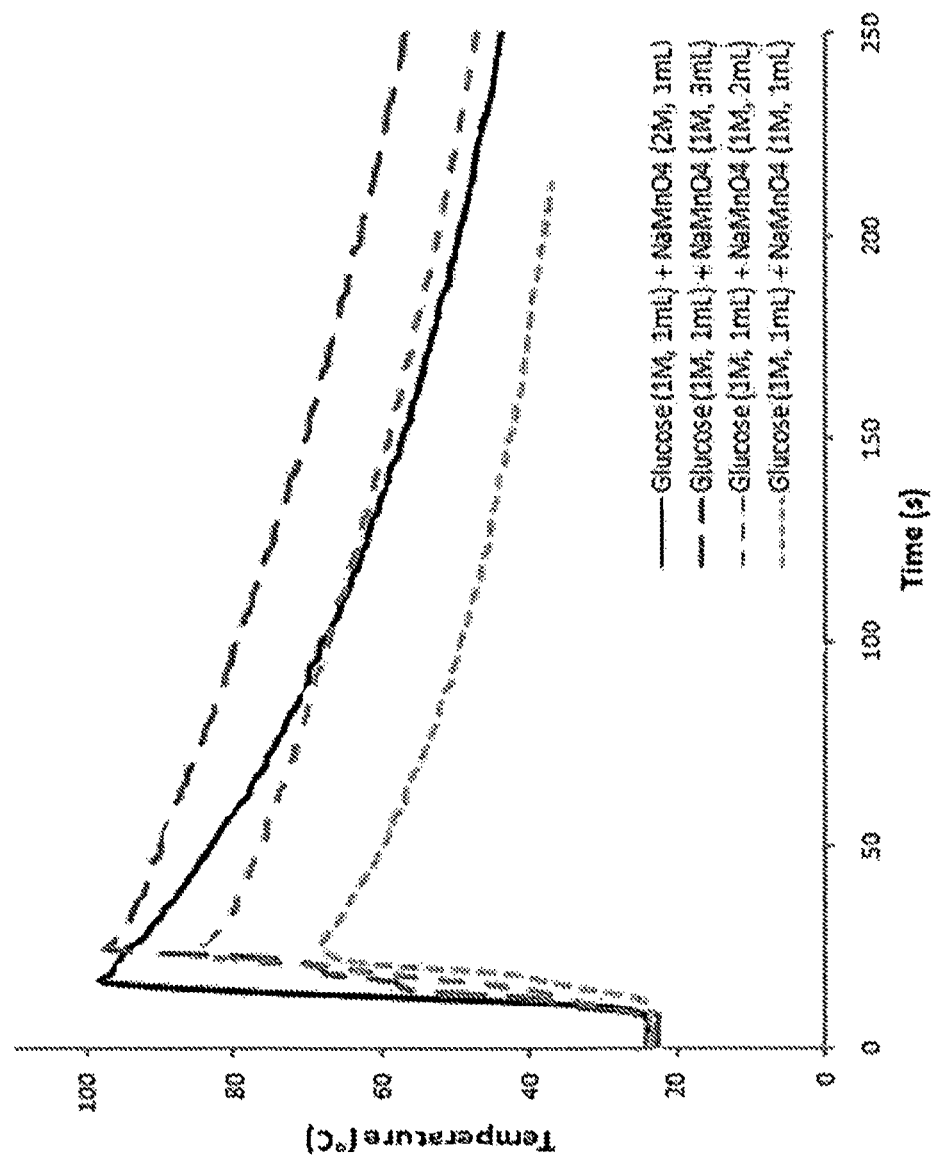
FIG. 12 is a graph plotting in vitro temperature profiles for simultaneous injection of the indicated amounts and concentrations of glucose and permanganate.

Using 1 mL of glucose (1M), the average maximum temperatures for simultaneous, glucose-first, and permanganate-first injections were 68.1, 82.9, and 66.3° C. respectively. When the volume of the permanganate solution (1M) was raised to 2 mL, the average maximum temperatures for simultaneous, glucose-first, and permanganate-first injections were 85.8, 90.7, and 88.4° C. respectively. Using 3 mL of permanganate solution (1M), the average maximum temperatures recorded for simultaneous, glucose-first, and permanganate-first injections were 97.9, 98.3, and 93.7° C. respectively. Increasing the volume of glucose solution to 2 mL led to a decline in average maximum temperatures for all three injection orders (53.9, 62.5, and 52.5° C.). When the concentration of the permanganate solution was raised to 2M, the average maximum temperatures for simultaneous, glucose-first, and permanganate-first injections were 100.0, 99.6, and 94.0° C. respectively. Averaged recordings for simultaneous injections of permanganate and glucose under various conditions are depicted in FIG. 12.

4. Sucrose vs. Permanganate

Figure 13:
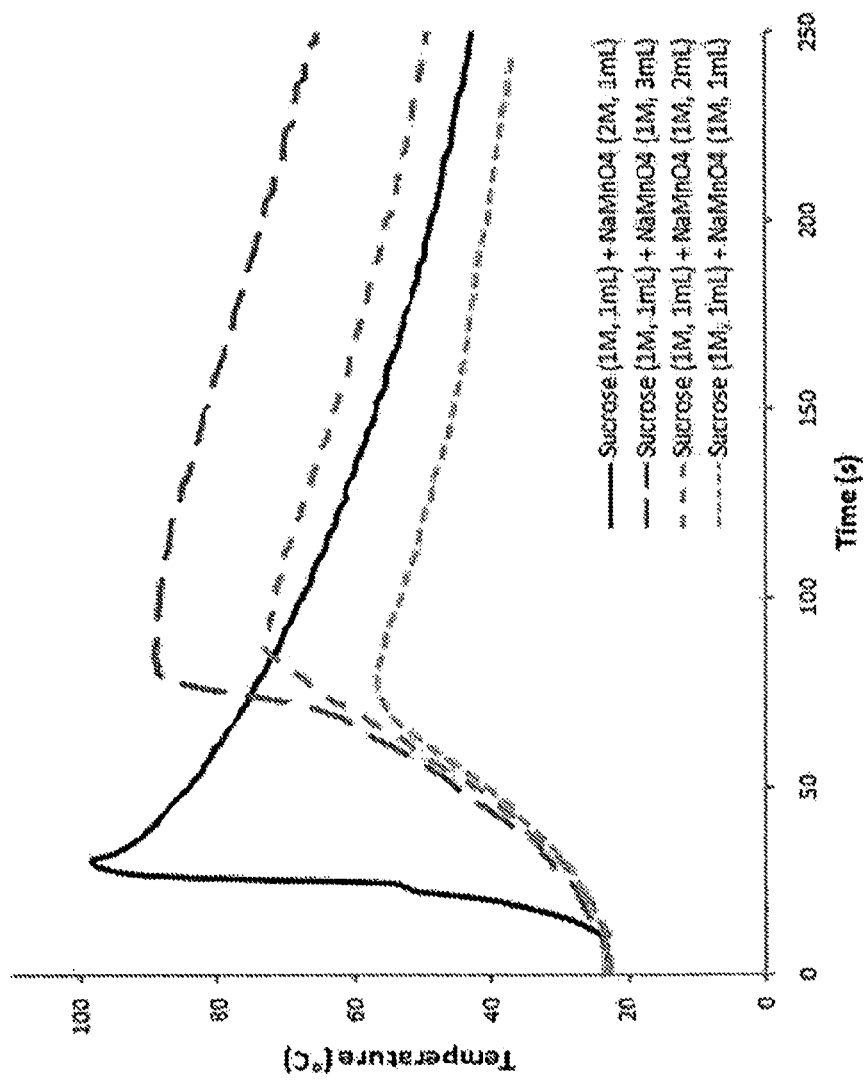
FIG. 13 is a graph plotting in vitro temperature profiles for simultaneous injection of the indicated amounts and concentrations of sucrose and permanganate.

Using 1 mL of sucrose (1M), the average maximum temperatures for simultaneous, sucrose-first, and permanganate-first injections were 56.8, 58.9, and 46.4° C. respectively. Raising the volume of permanganate solution (1M) to 2 mL, the average maximum temperatures for simultaneous, sucrose-first, and permanganate-first injections were 73.6, 82.1, and 64.9° C. respectively. Using 3 mL of permanganate solution (1M), the average maximum temperatures for simultaneous, sucrose-first, and permanganate-first injections were 90.1, 85.1, and 74.6° C. respectively. Increasing the volume of sucrose solution to 2 mL also led to a decline in average temperature increase for all three injection orders (45.9, 51.0, 44.6° C.). When the concentration of the sucrose solution (1 mL) was raised to 2M, the average maximum temperatures for simultaneous, sucrose-first, and permanganate-first injections were 100.2, 99.8, 100.0° C. respectively. Averaged recordings for simultaneous injections of permanganate and sucrose under various conditions are depicted in FIG. 13.

Figure 14:
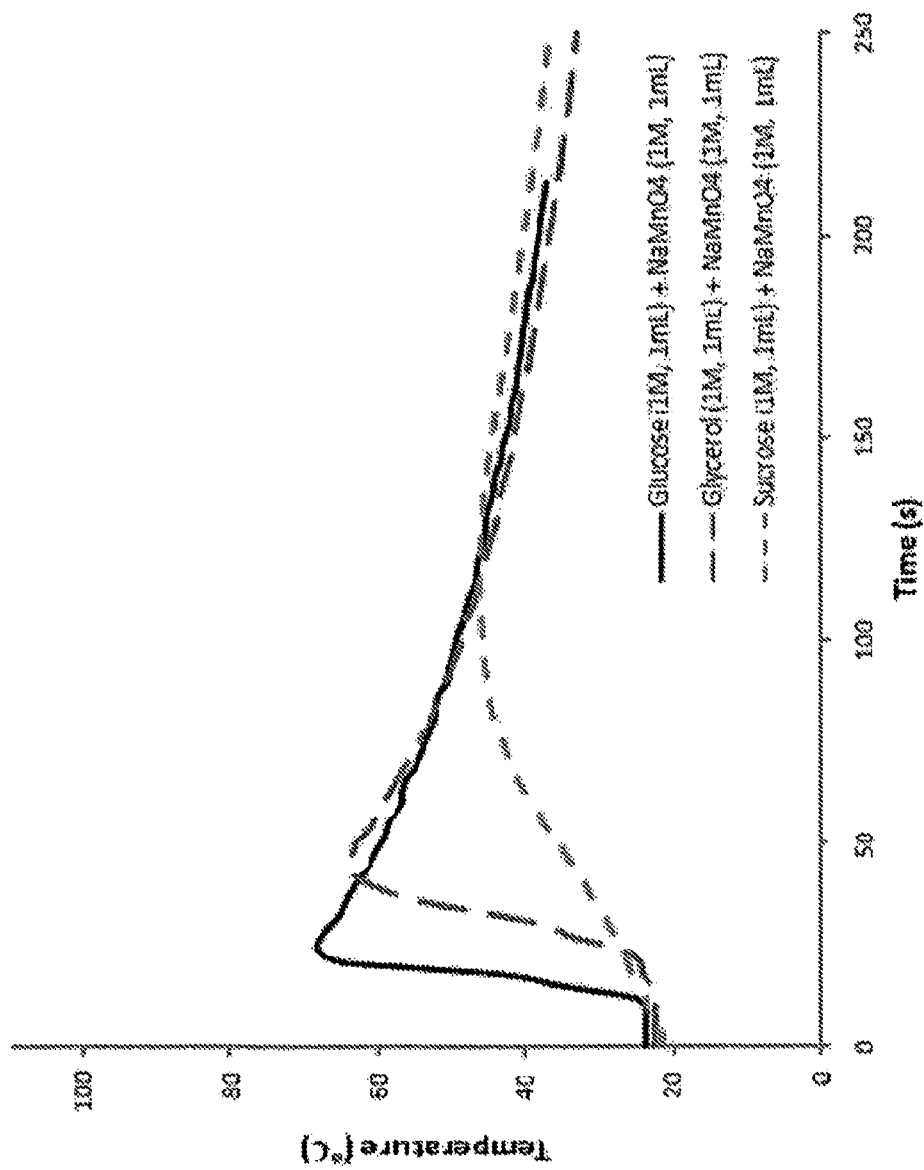
FIG. 14 is a graph plotting a summary of the in vitro results for glycerol, glucose, and sucrose with 1 M permanganate.
Figure 15:
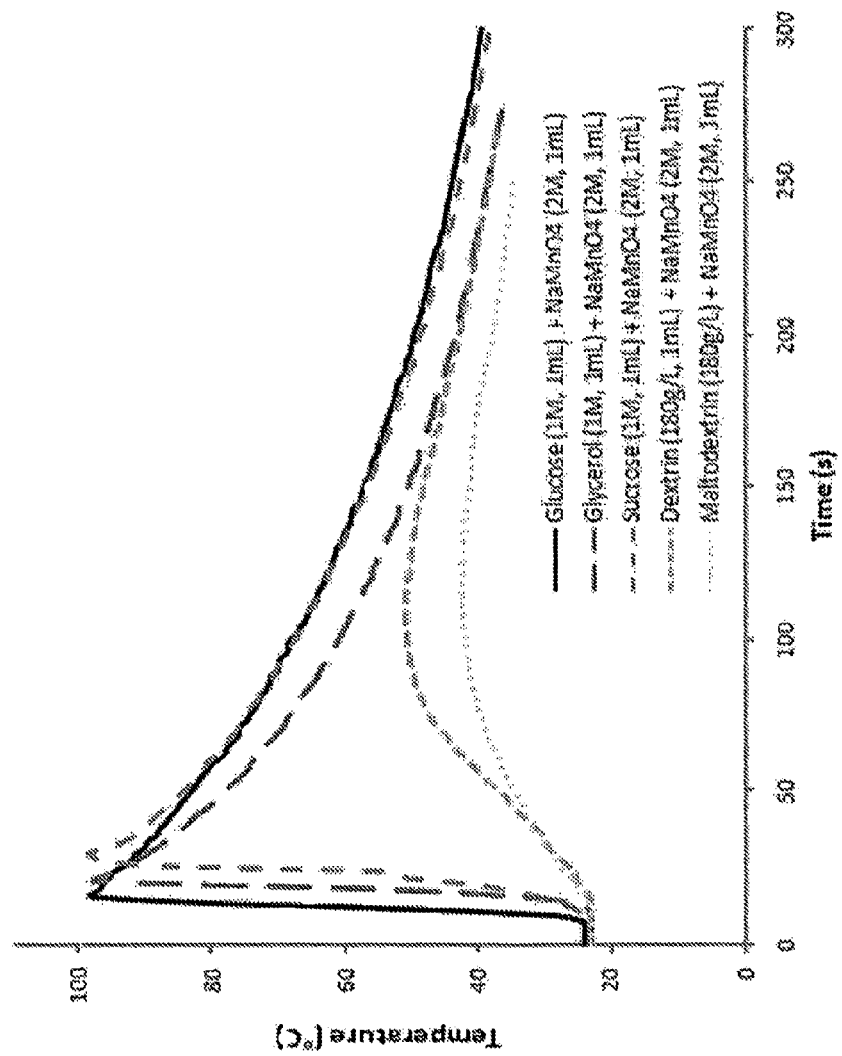
FIG. 15 is a graph plotting a summary of the in vitro results for glycerol, glucose, and sucrose with 2 M permanganate.

A summary of the results for glycerol, glucose, and sucrose, including the average temperature increases (maximum temperature—basal temperature) under various conditions, is presented in Table 1 and depicted in FIGS. 14 and 15. As can be seen in FIG. 14, using 1M permanganate, the rank of temperature increase achieved by different substrates from the highest to the lowest was glucose, glycerol, sucrose, dextrin and maltodextrin. This observation was in line with the observation that larger, more complex substrates tended to yield lower maximum temperatures. At least for the smaller substrates, however, the differences in maximum temperature and kinetics among the substrates were less pronounced when the concentration of the permanganate solution was increased to 2M (FIG. 15).

5. Oligosaccharides

Simultaneous injections of dextrin (180 g/L) and permanganate (1M, 1 mL) led to an average maximum temperature of 51.1° C. Under the same conditions except with maltodextrin as the substrate instead of dextrin, an average maximum temperature of 42.5° C. was observed. The peak of the temperature profile was also reached at a much slower rate for both dextrin and maltodextrin when compared to that of glycerol, glucose and sucrose.

6. Polysaccharides and Polyvinyl Alcohol vs. Permanganate

Multiple conditions for these substrates with permanganate were tested based on the best outcomes using glycerol, but none resulted in an increase of more than 8° C. from room temperature.

7. Ex vivo Injections

Figure 16:
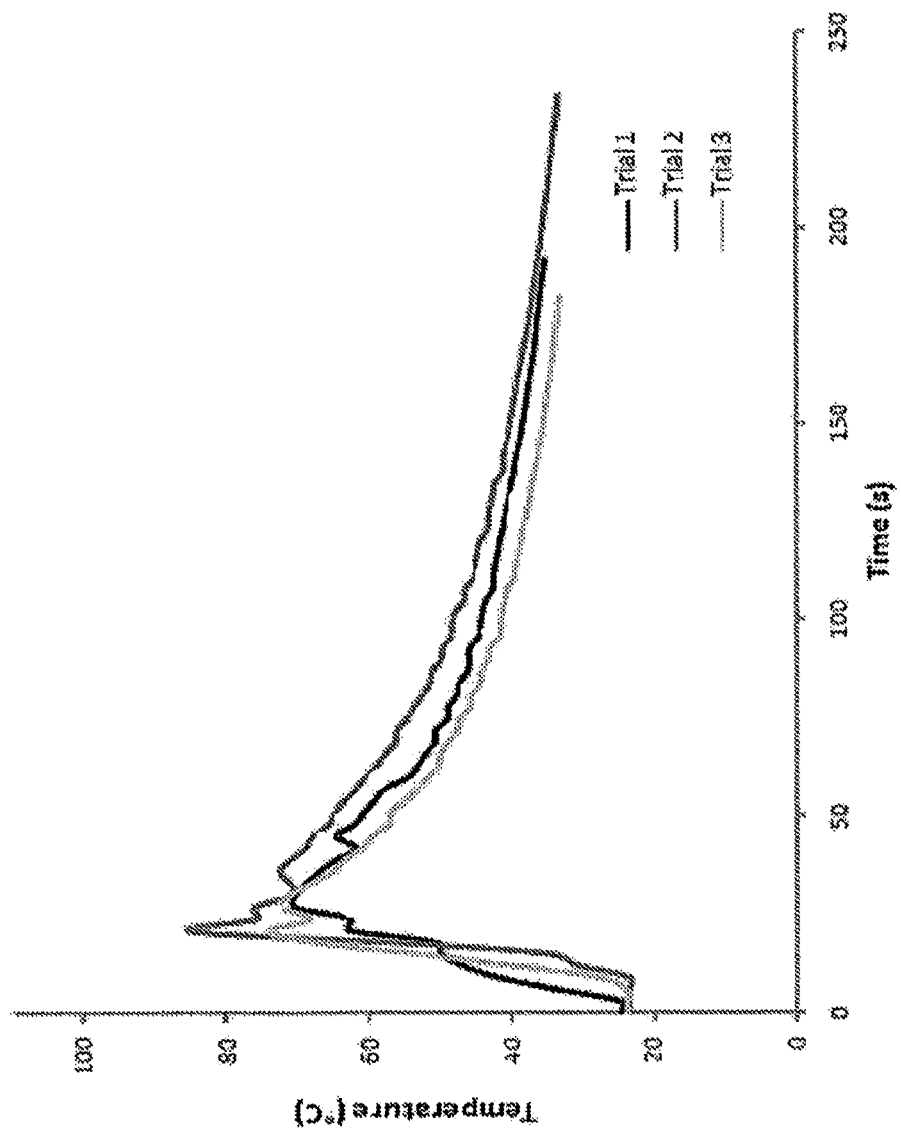
FIG. 16 is a graph plotting temperature profiles for ex vivo intramuscular injections of glucose and permanganate.
Figure 17:
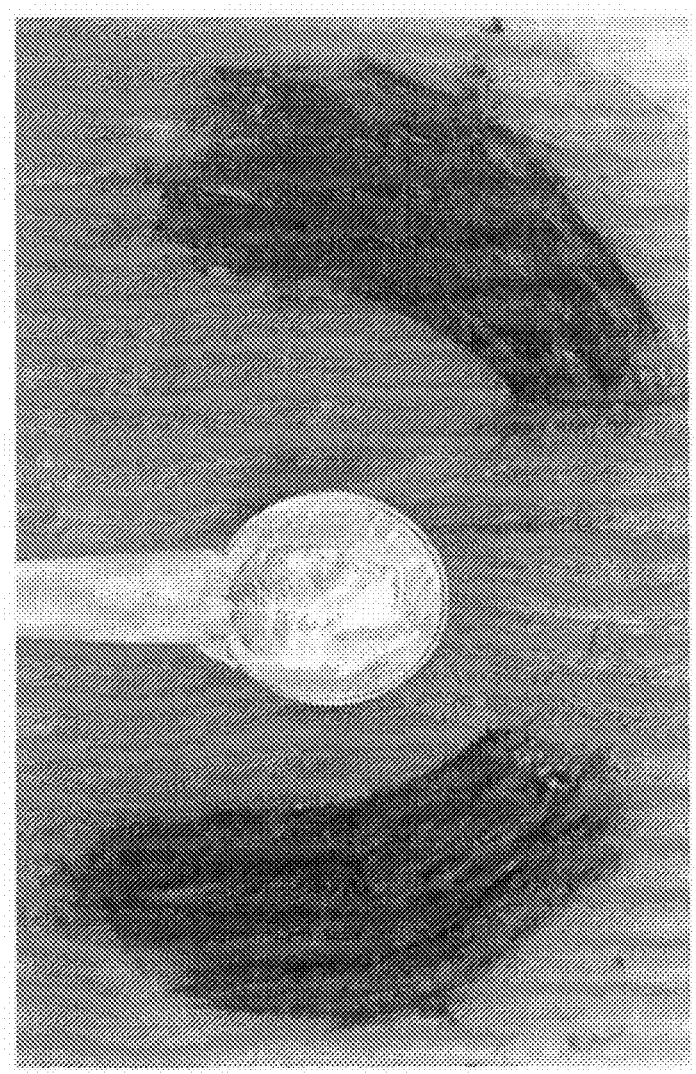
FIG. 17 is a picture of a gross specimen of an intramuscular injection, illustrating the staining due to reagents and products.

Simultaneous intramuscular injections of glucose (1M, 0.5 mL) and permanganate (2M, 0.5 mL) led to an average maximum temperature of 76.5° C. FIG. 16 shows the temperature recordings for three separate intramuscular injections. Tissue staining by permanganate and the presence of manganese dioxide obscured evaluation of lesions (FIG. 17). To appreciate the temperature gradient at the lesion site, an infrared image of the lesion site was taken after simultaneous injections of permanganate (2 M, 1 mL) and glucose (1 M, 1 mL) and sectioning the tissues after completion of the injection. A warm dime (1.79 cm diameter) was used as a size reference in the same focal plane. A maximum temperature of 58.2° C. in this ex vivo sample was recorded at the center of the lesion (saturated region). The temperature recorded at the periphery of the lesion was 19.8° C. It is noted that the actual maximum temperature might have been greater if not for the time delay and heat dissipation upon sectioning the lesion site.

measured using a plate reader at 570 nm. Only the live viable cells are able to convert yellow colored MTT reagent into purple colored formazan. Thus, any color changes observed in 96-well plates are reflective of the amount of cell death for each sample tested.

TABLE 1

Temperature increases and peak temperatures with different stoichiometries using glycerol, glucose, and sucrose.

| Reaction stoichiometry | | Average maximum temperature increase (° C.) | | | Average peak temperature (° C.) | | |
|---|---|---|---|---|---|---|---|
| | | Simultaneous | Substrate first | Permanganate first | Simultaneous | Substrate first | Permanganate first |
| Glycerol (1M/1 mL) | NaMnO4 (1M/1 mL) | 41.4 | 48.4 | 37.6 | 63.9 | 71.1 | 59.3 |
| | NaMnO4 (1M/2 mL) | 66.3 | 64.4 | 48.5 | 89.1 | 86.7 | 70.3 |
| | NaMnO4 (1M/3 mL) | 66.6 | 67.5 | 55.3 | 90.6 | 90.3 | 77.9 |
| | NaMnO4 (2M/1 mL) | 74.5 | 76.9 | 75.4 | 97.4 | 99.1 | 97.0 |
| Glucose (1M/1 mL) | NaMnO4 (1M/1 mL) | 44.4 | 60.2 | 43.9 | 68.1 | 82.9 | 66.3 |
| | NaMnO4 (1M/2 mL) | 62.6 | 68.6 | 66.3 | 85.8 | 90.7 | 88.4 |
| | NaMnO4 (1M/3 mL) | 75.2 | 77.3 | 71.6 | 97.9 | 98.3 | 93.7 |
| | NaMnO4 (2M/1 mL) | 76.2 | 76.8 | 70.6 | 100.0 | 99.6 | 94.0 |
| Sucrose (1M/1 mL) | NaMnO4 (1M/1 mL) | 33.5 | 37.1 | 24.9 | 56.8 | 58.9 | 46.4 |
| | NaMnO4 (1M/2 mL) | 51.0 | 60.0 | 42.1 | 73.6 | 82.1 | 64.9 |
| | NaMnO4 (1M/3 mL) | 66.9 | 63.0 | 51.5 | 90.1 | 85.1 | 74.6 |
| | NaMnO4 (2M/1 mL) | 77.0 | 77.7 | 76.7 | 100.2 | 99.8 | 100.0 |

Example 2

Effects of Urea and Ethanol on Human Tumor Cell Lines

1. Materials and Methods

Cell culture: HuH-7 cells were cultured in Dulbecco's modified Eagles medium (DMEM). The osteosarcoma cell line 143B and the breast cancer cell line MCF-7 were cultured in improved minimum essential medium (IMEM; Invitrogen, Carlsbad, Calif.). Cells were cultured in 75 cm$^2$ tissue culture flasks at a density of $3 \times 10^4$ cells/ml in the growth medium was supplemented with 10% fetal bovine serum (Atlanta Biologicals, Lawrenceville, Ga.), and 100 µg/ml penicillin/streptomycin (Invitrogen). All flasks were incubated at 37° C. with 5% CO$_2$. Cells were plated in 96-well plates for the MTT assays at a concentration of $3 \times 10^5$ cells per well overnight prior to performing the assays. Urea (Fluka, Buchs, Switzerland) and ethanol (Pharmco-Aaper, Shelbyville, Ky.) were added to cells in various concentrations as described below.

Cell viability assay: Cell viability assays were performed using as a substrate the MTT reagent 3-(4,5-Dimethylthiazol-2-yl)-2,5-diphenyltetrazolium bromide (Sigma-Aldrich, St. Louis, Mo.) at a concentration of 10 µg/100 µl. Growth medium was aspirated from the wells and cells were washed twice with 1×PBS. 200 µl growth medium containing either urea, ethanol, or urea and ethanol in combination at varying concentrations was added to each well and plates were incubated at 37° C. at three different time points: 2 hours, 6 hours and 24 hours, respectively. Every sample at each concentration of urea and ethanol was plated in triplicate for each time point tested. One hundred µl of MTT substrate was added to each well in a 96-well plate and plates were incubated for 1 hour at 37° C. Cells were then gently washed in 1×PBS and 100 µl stop solution (acidified phenol) was added to each well. Plates were incubated again at 37° C. for 30 minutes and the colorimetric changes in the cells were DNA Fragmentation Assay: 2 hours after the treatment with 1 M urea and incubation at 37° C., cells were harvested and resuspended in lysis buffer (10 mM Tris-HCl (pH 8.0) 5 mM EDTA, 100 mM NaCl, 1 mg proteinase K per ml, and 0.5% final concentration of SDS). Cell lysates were incubated at 37° C. for 3 hours, and the samples were centrifuged at 13,000 for 30 minutes. Supernatants containing DNA were extracted with phenol-chloroform and precipitated with ethanol. Equal amounts of DNA were resolved on a 2% agarose gel containing ethidium bromide, and bands corresponding to nucleosomes were visualized under ultra violet light.

2. Sensitivity of Human Tumor Cells to Urea at Low Concentrations

Figure 18:
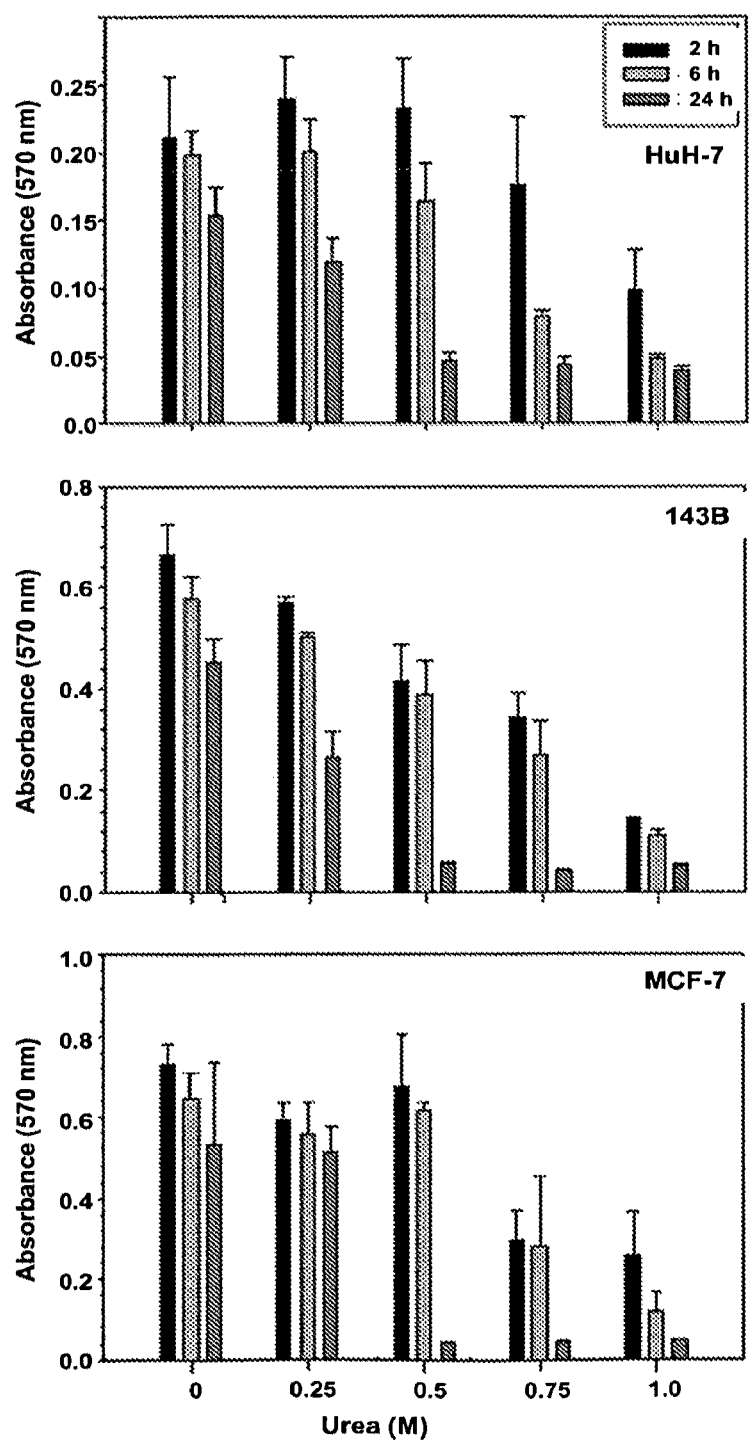
FIG. 18 is a series of graphs plotting absorbance of cell lysates at 570 nm as a measure of cell viability in studies to evaluate the cytotoxic effects of urea on human cancer cells. MTT (3-(4,5-Dimethylthiazol-2-yl)-2,5-diphenyltetrazolium bromide) assays were performed with HuH-7 (top panel), 143B (middle panel), and MCF-7 (bottom panel) cells in a time course experiment with varying concentrations of urea. X-axis data points are identical for all three cell lines. Data presented are mean+SD of triplicate samples for at least three independent experiments.

Urea is a natural cellular product of the TCA cycle produced by normal, healthy hepatocytes in the liver, and is excreted by the kidneys. Urea also is used as a protein denaturant. To determine whether urea can induce cell death of tumor cells, experiments MTT assays were performed using $9 \times 10^4$ HuH-7, 143B and MCF-7 cells with different concentrations of urea in a time course experiment. Interestingly, urea was toxic to these cells in the range of 250 mM to 1 M. 50% of the HuH-7 cells survived at 250 mM at 24 hours, whereas 500 mM urea was completely toxic to HuH-7 cells at this time point (FIG. 18). After a 6 hour exposure, about 50% of the cells survived with 750 mM urea in the growth medium. Similar results were obtained for 143B and MCF-7 cells (FIG. 18).

These data showed that urea is lethal at a concentration well below 1 M at shorter exposure times, and induces complete cell death at 500 mM after exposure for 24 hours, indicating that urea could be an effective cytotoxic drug at low concentrations.

3. Sensitivity of Tumor Cells to Ethanol

Figure 19:
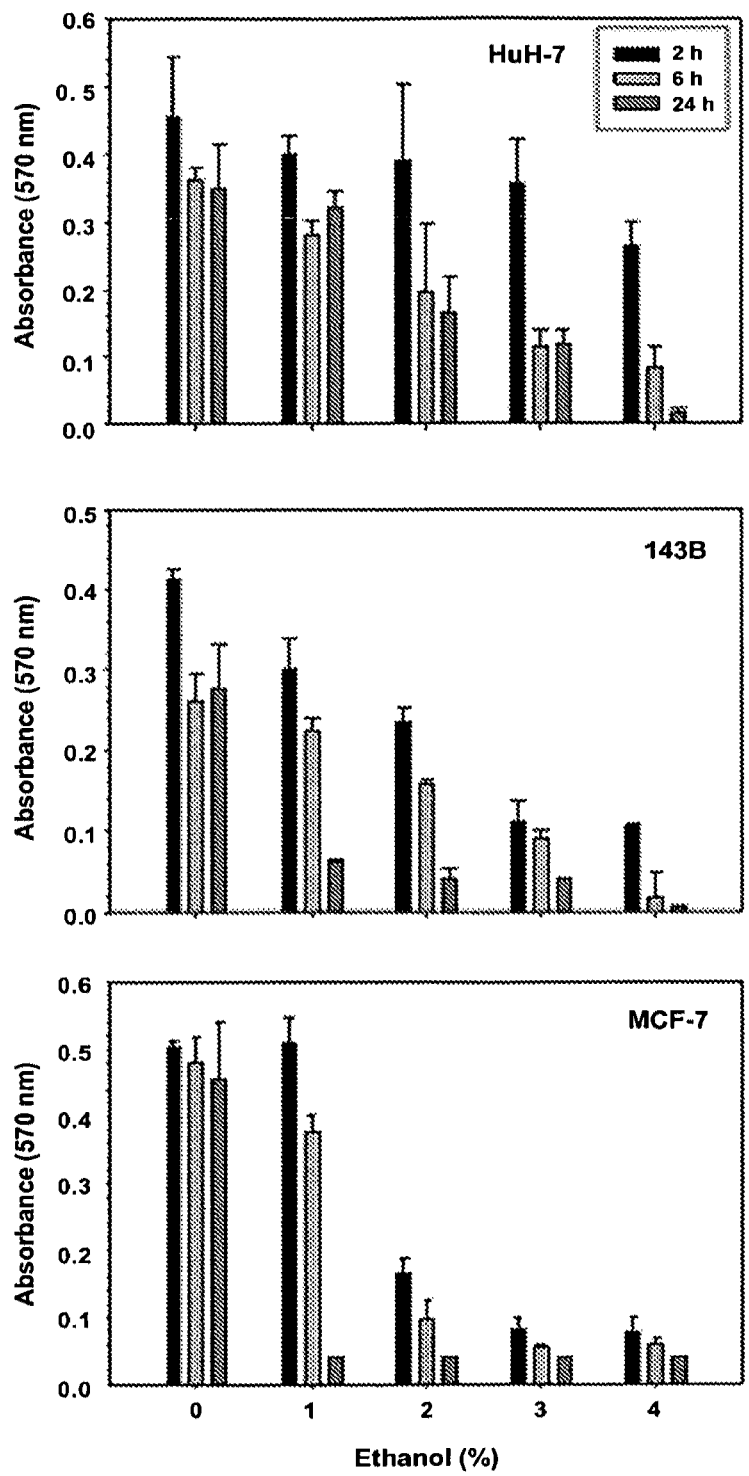
FIG. 19 is a series of graphs plotting absorbance of cell lysates at 570 nm as a measure of cell viability in studies to evaluate the cytotoxic effects of very low concentrations of ethanol on human tumor cell lines. A time course experiment was conducted with HuH-7 (top panel), 143B (middle panel), and MCF-7 (bottom panel) cell lines following exposure to ethanol at different concentrations (v/v). Data presented are mean+SD of triplicate samples for at least three independent experiments.

Similar to the studies with urea, the cytotoxicity of 5% to 40% (v/v) ethanol was tested. These studies showed that ethanol was toxic to HuH-7 cells at a concentration of 5% (v/v), results that are comparable to the cytotoxicity reported for HepG2 cells (Castaileda and Kinne (2000a) *J. Cancer Res. Clin. Oncol.* 126-503-510). In further experiments, the amount of ethanol exposure was lowered, revealing that ethanol was toxic to HuH-7 cells at an extremely low concentration of 3% (v/v; FIGS. 19), and 2% ethanol induced 50% cell death after 6 hours of exposure, while 4% ethanol was lethal at 2 hours. By comparison, ethanol was much more toxic to 143 B and MCF- 7 cells (FIG. 19). Cell death was>90% after exposure for 2 hours at 3% concentration, whereas>90% of cells died after a 24 hour exposure to 1% ethanol (FIG. 19). These results demonstrated that ethanol is a potent inducer of cytotoxicity when used at very low concentrations.

Figure 20:
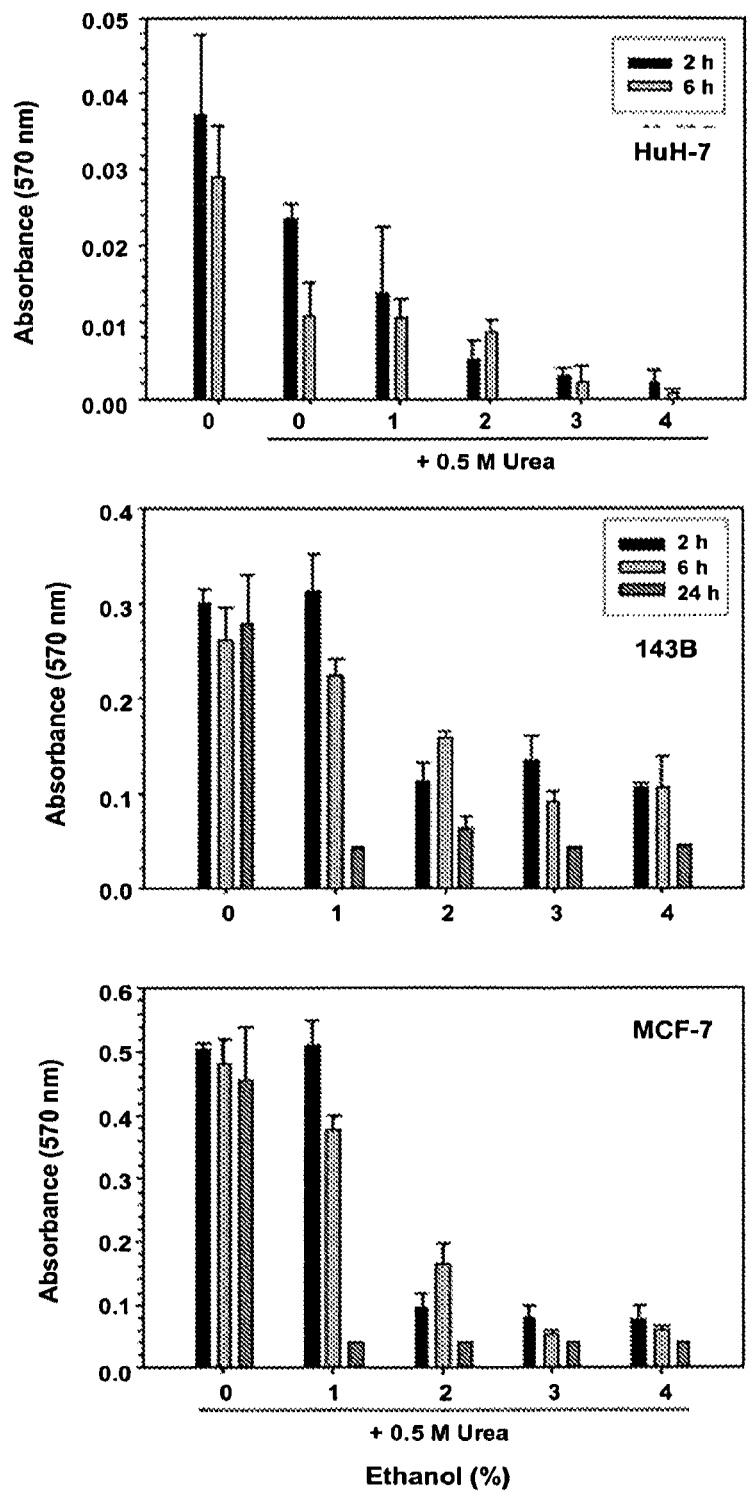
FIG. 20 is a series of graphs plotting absorbance of cell lysates at 570 nm as a measure of cell viability in studies to evaluate the effects of urea and ethanol on human tumor cell lines. MTT assays were performed in a time course experiment using 0.5 M urea with varying concentrations of ethanol, as indicated. X-axis data points are identical for 143B (middle panel) and MCF-7 (bottom panel) cells. HuH-7 cells (top panel) were tested exactly as the other two cell lines at 2 hour and 6 hour exposure times. Data presented are mean+SD of triplicate samples for at least three independent experiments.
Figure 21:
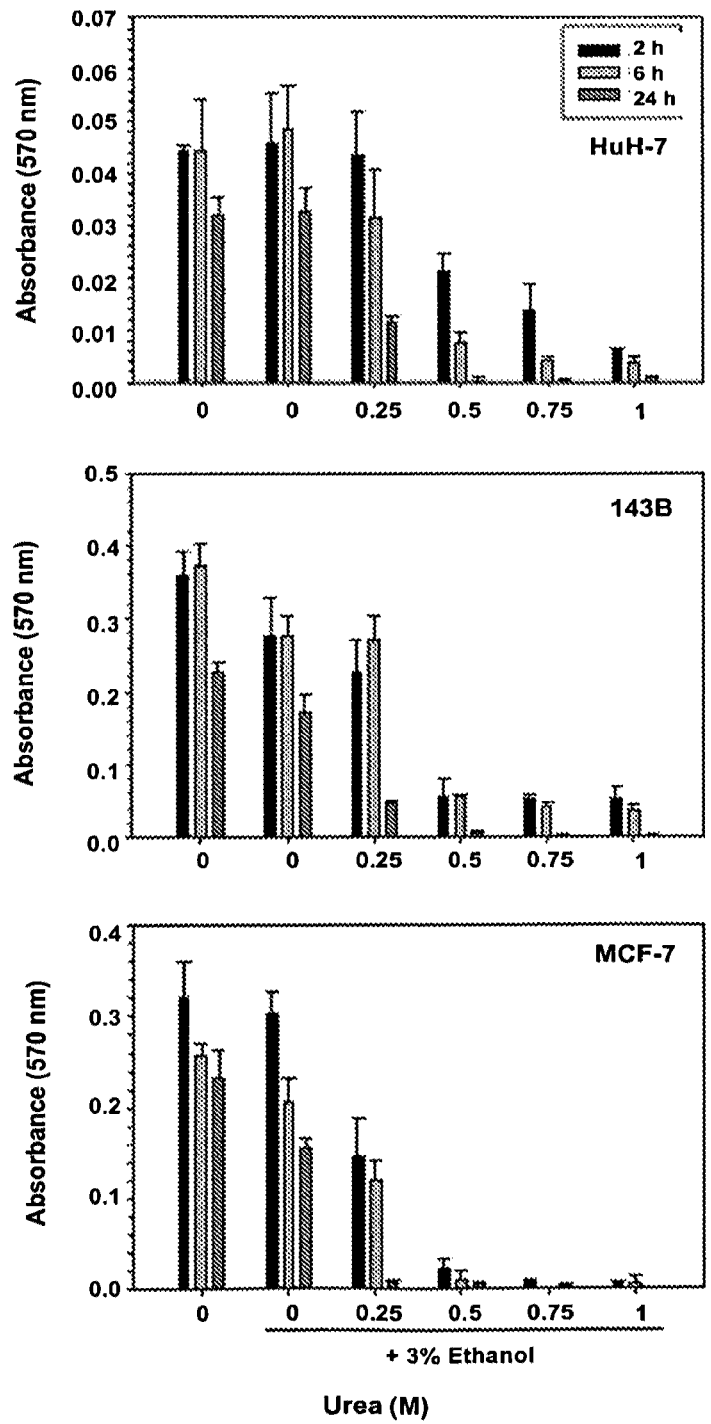
FIG. 21 is a series of graphs plotting absorbance of cell lysates at 570 nm as a measure of cell viability in studies to evaluate the effect of varying concentrations of urea on human tumor cells exposed to 3% ethanol. X-axis data points are identical for all three cell lines tested (HuH-7, top panel; 143B, middle panel; MCF-7, bottom panel). Data presented are representative of at least three independent experiments, and are mean+SD of triplicate samples.

4. Millimolar Concentrations of Urea and Ethanol in Combination Induce Cell Death Following the observation that low concentrations of urea and ethanol were toxic to HuH-7, 143 B and MCF-7 cells, experiments were conducted to test whether both compounds together could enhance cell death. These studies were performed using a fixed concentration of either urea or ethanol that caused 50% cell death. As shown in FIG. 20, a fixed concentration of 0.5 M urea and varying concentrations of ethanol (0 to 4% (v/v)) induced total cell death within 2 hours of exposure. This result was different from that with ethanol alone (FIG. 21), demonstrating that urea exacerbates cell death when used in combination with ethanol. On the other hand, a fixed concentration of ethanol at 3% and varying concentrations of urea (0 to 1 M) had an effect similar to that of urea alone (FIG. 21), suggesting that the addition of ethanol to the growth medium does not enhance cell death. Collectively, these data show that, when used in combination, urea plays a major role in enhancing cytotoxicity and exacerbating cell death.

5. Urea Induces Apoptosis in Tumor Cell Lines

Figure 22:
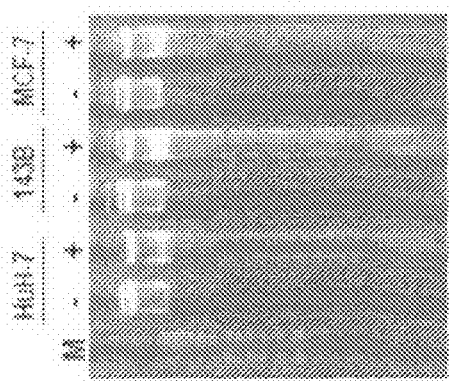
FIG. 22 is a picture of a gel containing DNA from HuH-7, 143B and MCF-7 human tumor cell lines treated with (+) or without (−) 2 M urea, indicating apoptosis after treatment. Total DNA was isolated from cells and resolved on a 2% agarose gel. Lane M is a 100 by ladder.

It has been reported that ethanol induces apoptosis in HepG2 cells (Castañeda and Kinne (2000a, supra); and Castañeda and Kinne (200b) *J. Cancer. Res. Clin. Oncol.* 126: 305-310). To test whether urea also induces apoptosis, a DNA fragmentation assay was performed using each of the three cell lines treated with 1 M urea for 2 hours. Chromosomal DNA was isolated from the cells, and the extent of damage was analyzed by DNA laddering, a hallmark of apoptosis. As shown in FIG. 22, urea induced apoptosis in all three cell lines, causing the formation of low molecular weight DNA by generating a nucleosomal pattern. A similar result was observed with 143B and MCF-7 cells upon exposure to 10% ethanol for 6 hours. Collectively, these results suggest that both urea and ethanol induce apoptotic cell death when used in combination.

Example 3

Thermochemical Ablation in a Rodent Model

1. Materials and Methods

Device Preparation: A miniature device was created by placing two 18 G blunt fill needles (BD™, Franklin Lakes, N.J.) through a septum cap (Baxter INTERLINK® injection site; Baxter, Deerfield, Ill.) such that the tip of each needle extended just beyond the terminus of the male Luer lock adapter. Subsequently, a cyanoacrylate polymer (LOCTITE® super glue; Henkel Consumer Adhesives, Inc., Avon, Ohio) was injected into the innermost chamber of the septum cap in such a way as to obliterate the dead space but not plug the needles. This was accomplished by loading a syringe with cyanoacrylate, inserting the needle through and just beyond the septum cap, filling the void with monomer and injecting slowly to minimize air bubble formation. The injection was halted when the cyanoacrylate was even with the end of the male Luer lock adapter and the injecting needle was removed. Care was taken so that the two blunt fill needles were not blocked with cyanoacrylate. The device was then left for a period of 24 hours to allow for polymerization.

Magnetic Resonance Compatible Device: The miniature device was created by placing two 18 G I.V. catheters (BD INSYTE™ AUTOGUARD™ shielded I.V. catheters; BD™) through a septum cap such that the opening of each catheter extended beyond the terminus of the Luer lock adapter and injecting a cyanoacrylate polymer into the inner portion of the septum cap as for the basic device. During the process of filling the injection site with glue and allowing the glue to polymerize, it was found to be important for the needle to remain inside of the catheter. If the needles were removed prematurely, catheters tended to soften and become tortuous. The device was left for a period of 24 hours to allow for polymerization.

Priming Volumes: To determine the priming volume of both the miniature device and the MR miniature device, they were each connected to extension tubing (Baxter Extension Sets; Baxter). The extension sets and 18 G blunt fill needles and 18 G I.V. catheters of the devices were then primed with saline solution. After thoroughly drying the tips of the 18 G needles and catheters, both devices were coupled with a 22 G hypodermic needle (Kendall MONOJECT™ hypodermic needle with polypropylene hub; Covidien, Mansfield, Mass.) and a 22 G I.V. catheter, respectively. A 1 mL syringe with saline solution was then used to determine the priming volumes of the devices. The use of 1 mL syringes allowed measurement to the nearest hundredth of a milliliter.

Injections: Injections were performed using a dual syringe pump (Standard Infusion Only Harvard Pump 11 Plus Dual Syringe Pump; Harvard Apparatus, Holliston, Mass.) at an injection rate of 1.5 cc/minute. Thawed porcine liver was brought to room temperature prior to use.

Injections were conducted using 11 M hydrochloric acid (HCl) and 11 M sodium hydroxide (NaOH). Temperature measurements were obtained using a thermocouple thermometer (COLE-PARMER® DIGI-SENSE® DUAL-LOGR™; Cole-Parmer Instrument Company, Vernon Hills, Ill.) using a 3 cm 23 G Type T thermocouple temperature probe (Physitemp Instruments, Clifton, N.J.). For each injection, the needle was inserted into the liver tissue at an oblique angle. The device entered near the center of the lobe, with the opening of the needle becoming close to the periphery of the lobe to minimize chances of injecting into vascular structures. In order to ensure close proximity of the needle tip and thermocouple thermometer, they were inserted simultaneously with the tips less than one millimeter apart prior to insertion. Upon completion of injections, 2 mm slices of liver were obtained using a meat slicer (Savoureux PRO LINE™ meat slicer; Heartland American, Chaska, Minn.). Samples were cooled to make the tissue firm for sectioning.

Lesion Volume: Lesion volumes were estimated by summing the individual slice volumes, which were determined by surface area of the coagulation zone of each slice (ImageJ, freely available from the NIH) and multiplying by the slice thickness.

2. Device Priming Volumes

Three trials were performed with each device to find priming volumes of three miniature device and three MR miniature devices. The miniature devices had an average priming volume of 0.03±0.01 mL, while the MR version had an average priming volume of 0.05±0.01 mL.

3. Thermochemical Ablation and Lesions

Figure 23:
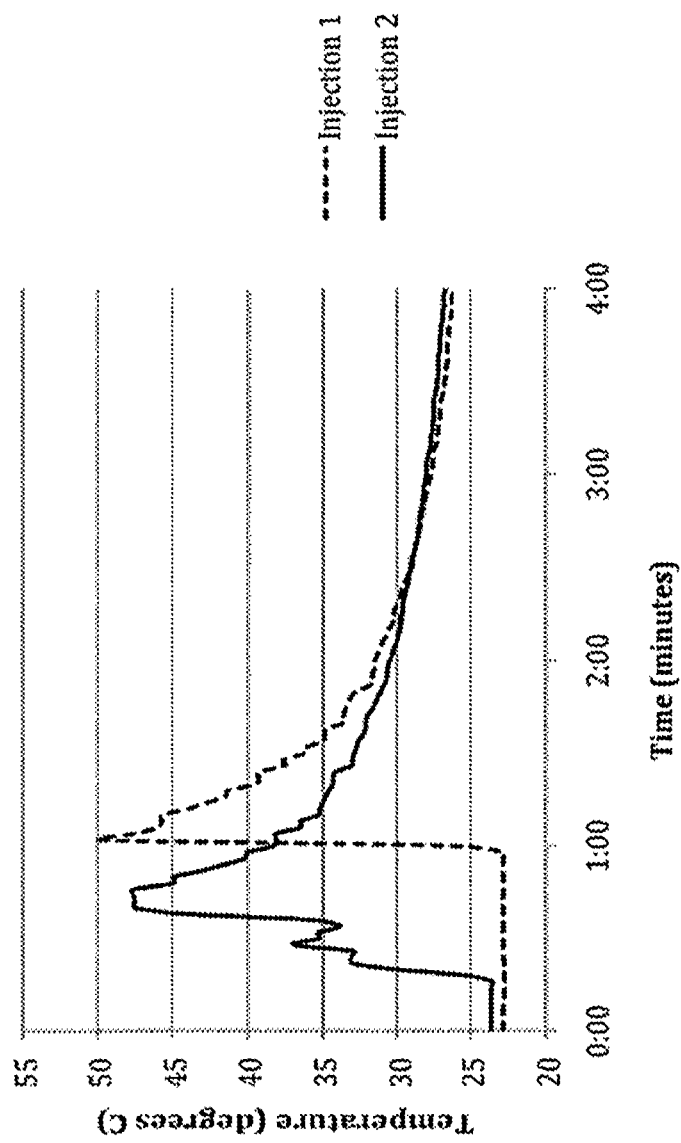
FIG. 23 is a graph plotting temperature profiles for simultaneous injection of 0.27 mL each (Injection 1) or 0.54 mL each (Injection 2) of hydrochloric acid and sodium hydroxide into porcine liver.

Two injections were performed—the first with 0.27 mL of 11 M HCl and 0.27 mL of 11 M NaOH, and the second with 0.52 mL of 11 M HCl and 0.52 mL of 11 M NaOH. Temperature data are presented in FIG. 23. Each injection created a fairly well-demarcated zone of coagulation.

Given the above, it is clear that thermochemical ablation can be conducted on a miniature scale. Devices as described in the present example also are useful with redox reagents and denaturing agents, for example.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A chemical ablation system, comprising:
   a percutaneous fluid delivery cannula comprising a lumen extending from a proximal-most opening to a distal portion, the distal portion comprising a port in fluid communication with the lumen; and
   a reservoir defining an internal chamber containing a mixture of denaturing reagents, wherein a fluid output of the internal chamber of the reservoir is connected to the proximal-most opening of the lumen and in fluid communication with the lumen of the percutaneous fluid delivery cannula such that the denaturing reagents are contemporaneously deliverable through the proximal-most opening of the lumen and out of the port so as to denature components of cells present at the targeted site to locally ablate bodily tissue proximate the distal portion of the percutaneous fluid delivery cannula.

2. The system of claim 1, wherein the combination of reagents comprises urea and ethanol.

3. The system of claim 2, wherein the urea has a concentration of about 0.2 M to about 2 M.

4. The system of claim 2, wherein the urea has a concentration of about 0.25 M to about 0.5 M.

5. The system of claim 2, wherein the ethanol is about 0.5% to about 3% ethanol.

6. The system of claim 2, wherein the ethanol is about 1% to about 2% ethanol.

7. The system of claim 1, further comprising a real-time imaging system that monitors the distal portion of the percutaneous fluid delivery cannula and the delivery of the reagent.

8. The system of claim 1, wherein the percutaneous fluid delivery cannula comprises a generally rigid injection needle.

9. The system of claim 8, wherein the injection needle comprises an outside diameter of about 0.134 inches or less.

10. The system of claim 1, wherein the percutaneous fluid delivery cannula comprises a flexible catheter.

11. A method for chemical ablation of targeted tissue, comprising:
    delivering two or more denaturants through a proximal-most opening of a lumen of a single-chamber percutaneous injection needle to a targeted tissue site while a distal tip portion of the single-chamber percutaneous injection needle is positioned at the targeted tissue.

12. The method of claim 11, further comprising connecting the proximal-most opening of the lumen of the single-chamber percutaneous injection needle to a reservoir containing a combination of said two or more denaturants, wherein the denaturants are delivered simultaneously from an internal space of the reservoir through the proximal-most opening of the lumen of the single-chamber percutaneous injection needle and out from one or more side ports at the distal tip portion of the single-chamber percutaneous injection needle.

13. The method of claim 11, wherein said delivering comprises sequentially delivering said two or more denaturants through the proximal-most opening of the lumen of the single-chamber percutaneous injection needle and out from one or more side ports at the distal tip portion of the single-chamber percutaneous injection needle, a first denaturant of said two or more denaturants being delivered from an interior space of a first reservoir and through the proximal-most opening of the lumen, and a second denaturant of said two or more denaturants being delivered from an interior space of a second reservoir that is different from the first reservoir and through the proximal-most opening of the lumen, wherein the first and second denaturants are delivered from one or more side ports of the injection needle.

14. The method of claim 11, wherein the denaturants comprise urea and ethanol.

15. The method of claim 14, wherein the urea has a concentration of about 0.2 M to about 2 M.

16. The method of claim 14, wherein the urea has a concentration of about 0.25 M to about 0.5 M.

17. The method of claim 14, wherein the ethanol is about 0.5% to about 3% ethanol.

18. The method of claim 14, wherein the ethanol is about 1% to about 2% ethanol.

19. The method of claim 11, wherein the denaturants further comprise a diagnostic group usable for imaging or tracing purposes.

20. The method of claim 11, wherein the denaturants comprise one or more diagnostic leaving groups usable for imaging or tracing purposes.

* * * * *